United States Patent [19]

Caufield et al.

[11] Patent Number: 5,242,945
[45] Date of Patent: Sep. 7, 1993

[54] TETRONIC AND THIOTETRONIC ACID DERIVATIVES AS PHOSPHOLIPASE A$_2$ INHIBITORS

[75] Inventors: Craig E. Caufield, Plainsboro, N.J.; James M. Rinker, Reading, Pa.

[73] Assignee: American Home Products Corporation, New York, N.Y.

[21] Appl. No.: 685,265

[22] Filed: Apr. 12, 1991

[51] Int. Cl.$^5$ ............... A61K 31/365; A61K 31/38; C07D 307/33; C07D 333/32
[52] U.S. Cl. .................. 514/473; 514/445; 514/826; 549/64; 549/65; 549/313; 549/314; 549/316; 549/317
[58] Field of Search .............. 549/64, 65, 66, 318, 549/313, 314, 315, 317, 316; 514/473, 474, 445, 826

[56] References Cited

U.S. PATENT DOCUMENTS 4,874,782  10/1989  Bonjouklian et al. ............... 549/313

FOREIGN PATENT DOCUMENTS 4969659  7/1974  Japan ................................. 549/318
51-1633  1/1976  Japan ................................. 549/318
62-19582  1/1987  Japan ................................. 549/64
1276061  6/1972  United Kingdom ............... 549/318

OTHER PUBLICATIONS

Kataoka, et al., *Chemical Abstracts* 84:175, 144m, English abstract of Japanese patent 51-1633, p. 174 (1976).
Omo et al., *Chemical Abstracts* 81:151976w, English abstract of Japanese patent 49-69659, pp. 510-511 (1974).
Foye, "Principles of Medicinal Chemistry," 2nd ed., pp. 80-83 Lea & Febiger, Philadelphia (1981).
B. Potts et al., *J. Am. Chem. Soc.*, 114, pp. 5093-5100 (1992).
"The Pharmacological Basis of Therapeutics", A. Gillman et al. ed., 6th ed., pp. 685, 1979-1480, and 1489-1490, MacMillan Publishing Co., New York (1980).
Remington's "Pharmaceutical Sciences," J. Hoover ed., 14th ed., Mack, pp. 1163-1173 Publishing Co., Easton, Penn. (1970).
L. Reynolds, et al., *J. Am. Chem. Soc.*, "Phospholipose A$_2$ Inhibition and Modification by Monoalogue," 110, pp. 5172-5177 (1988).
L. Reynolds, et al., *J. Biol. Chem.*, "Inhibition of Venom Phospholipose A$_2$ by Monolide and Manoalogue," 266 (75), 16512-16517 (1991).
C. Bennett et al., *Biochem. Pharmacol.*, "Differential Effect of Manolide on Secreted and Intracellular Properties," 36 (5), pp. 733-740 (1987).
Nemura et al. *Chem. Bull. Pharm.*, 34(12), 5188-90 (1986).
Tanaka et al. *Chem. Bull. Pharm.*, 27(8), 1901-1906 (1978).

*Primary Examiner*—Mark Russell
*Attorney, Agent, or Firm*—George Tarnowski

[57] ABSTRACT

There are disclosed compounds of the formula:

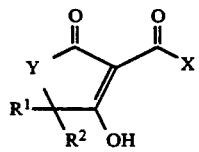

wherein
X is —CH$_2$R;
R is

—(CH$_2$)$_a$(CH=CHCH$_2$)$_c$(CH$_2$)$_d$CH$_3$, —(CH$_2$)$_b$R$^3$,

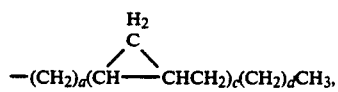

—CH$_2$)$_a$(C≡CCH$_2$)$_c$(CH$_2$)$_d$CH$_3$, —(CH$_2$)$_b$OR$^3$,

—(CH$_2$)$_b$SR$^3$, —(CH$_2$)$_b$NHR$^3$, —O(CH$_2$)$_b$R$^3$,

-continued

—S(CH$_2$)$_b$R$^3$, 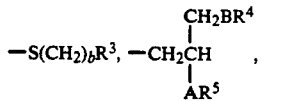

—(CH$_2$)$_b$CH=CHR$^3$, (CH$_2$)$_b$OR$^4$, and further when Y=S, R may also be —(CH$_2$)$_e$CH$_3$;
Y is —O— or —S—;
R$^1$ and R$^2$ are each, independently, hydrogen or lower alkyl;
R$^3$ is indolyl, furyl, phenyl or phenyl optionally mono- or disubstituted independently by alkyl of 1-7 carbon atoms, —C(CH$_3$)$_3$, —C(CH$_3$)$_2$CH$_2$C(CH$_3$)$_3$, —C(CH$_3$)$_2$CH$_2$CH$_3$, haloloweralkyl, perfluoroalkyl, lower alkoxy, aryl alkoxy, halo or nitro;
R$^4$ and R$^5$ are, independently, —COCH$_2$R$^7$, —CO$_2$R$^7$, —CONHR$^7$, geranyl or CH$_2$R$^3$;
R$^6$ is hydrogen or lower alkyl;

R$^7$ is geranyl and any moiety selected from R other than

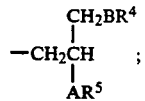;

A and B are, independently, —O—, —S— or —NR$^6$—; and
a is 0-8;
b is 1-10 when Y=S, and 2-10 when Y=O;
c is 1-3;
d is 0-9; and
e is 3-18;

which by virtue of their ability to inhibit PLA$_2$, are of use as antiinflammatory agents and there is also disclosed a method for the treatment of immunoinflammatory conditions, such as allergy, anaphylaxis, asthma and inflammation in mammals.

37 Claims, No Drawings

TETRONIC AND THIOTETRONIC ACID DERIVATIVES AS PHOSPHOLIPASE A₂ INHIBITORS

The present invention is directed to certain tetronic acid derivatives having anti-inflammatory activity and to a method for using them as anti-inflammatory agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides PGG₂ and PGH₂ by the cyclooxygenase pathway of arachidonic acid metabolism. These endoperoxides are also the precursors of the thromboxanes (Tx) A₂ and B₂. TxA₂ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin (PGI₂), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287–299 (1984)]. This is through their vasodepressor activities, participation in pain and fever and augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes B₄, C₄ and D₄. The substance denominated slow-reacting substance of anaphylaxis (SRS-A) has been shown to consist of a mixture of leukotrienes, with LTC₄ and LTD₄ as the primary products and having varying amounts of other leukotriene metabolites [see Bach et al., *J. Immun.*, 215, 115–118 (1980); *Biochem. Biophys. Res. Commun.*, 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that LTC₄ and LTD₄ are potent bronchoconstrictors of the human bronchi [see Dahlen et al., *Nature*, 288, 484–486 (1980)], and another leukotriene, LTB₄, is a powerful chemotactic factor for leukocytes [see A. W. Ford-Hutchinson, *J. Roy Soc. Med.*, 831–833 (1981)]. The activity of leukotrienes and slow-reacting substances as mediators of inflammation and hypersensitivity is extensively reviewed in Bailey and Casey, *Ann. Reports Med. Chem.*, 17, 203–207 (1982).

Phospholipase A₂ (PLA₂) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkylarachidonoyl-glycerophosphatidylcholine is acted upon by the PLA₂ the generation of platelet activating factor (PAF) is initiated; PAF is pro-inflammatory in its own right [see Wedmore et al., *Br. J. Pharmacol.*, 74, 916–917 (1981)]. In this regard it may be noted that the anti-inflammatory steroids are thought to inhibit eicosanoid synthesis by inducing the synthesis of a PLA₂ inhibitory protein denominated macrocortin or lipomodulin [see Flower et al., *Nature, London* 278, 456 (1979) and Hirata et al., *Proc. Natn. Acad. Sci., U.S.A.*, 77, 2533 (1980)].

As the initial step leading to subsequent conversion of AA to the various eicosanoids by the cyclooxygenase and lipoxygenase pathways, the PLA₂-mediated release of AA from membrane phospholipids is a critical event in attempting to deal with the various physiological manifestations which are based on the activity of the eicosanoids and/or PAF. Thus, while PLA₂ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Throm. Res.*, 3, 89 (1978)], the inhibition of PLA₂ is indicated in the therapeutic treatment of both PAF induced or cyclooxygenase and/or lipoxygenase pathway product-mediated physiological conditions. Thus, PLA₂ inhibitors are a rational approach to the prevention, removal or amelioration of such conditions as allergy, anaphylaxis, asthma and inflammation.

The invention provides novel compounds of the formula

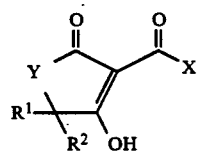

wherein
X is —CH₂R;
R is

—(CH₂)$_d$(CH=CHCH₂)$_c$(CH₂)$_d$CH₃, —(CH₂)$_b$R³,

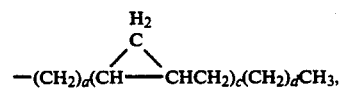

—CH₂)$_d$(C≡CCH₂)$_c$(CH₂)$_d$CH₃, —(CH₂)$_b$OR³,

—(CH₂)$_b$SR³, —(CH₂)$_b$NHR³, —O(CH₂)$_b$R³,

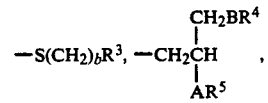

—(CH₂)$_b$CH=CHR³, (CH₂)$_b$OR⁴, and further when Y=S, R may also be —(CH$_2$)$_e$CH$_3$;

Y is —O— or —S—;

R$^1$ and R$^2$ are each, independently, hydrogen or lower alkyl;

R$^3$ is indolyl, furyl, phenyl or phenyl optionally mono- or disubstituted independently by alkyl of 1-7 carbon atoms, —C(CH$_3$)$_3$, —C(CH$_3$)$_2$CH$_2$C(CH$_3$)$_3$, —C(CH$_3$)$_2$CH$_2$CH$_3$, haloloweralkyl, perfluoroalkyl, lower alkoxy, aryl alkoxy, halo or nitro;

R$^4$ and R$^5$ are, independently, —COCH$_2$R$^7$, —CO$_2$R$^7$, —CONHR$^7$, geranyl or CH$_2$R$^3$;

R$^6$ is hydrogen or lower alkyl;

R$^7$ is geranyl and any moiety selected from R other than

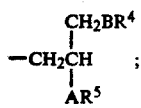

A and B are, independently, —O—, —S— or —NR$^6$—; and a is 0-8;

b is 1-10 when Y=S, and 2-10 when Y=O;

c is 1-3;

d is 0-9; and e is 3-18.

The invention further provides a method for treating immunoinflammatory conditions such as allergy, anaphylaxis, asthma and inflammation, in mammals, which comprises administering to a mammal so afflicted an effective amount of a compound having the formula

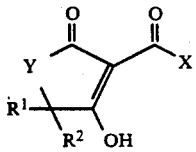

wherein

Y is —O— or —S—;

X is —(CH$_2$)$_a$CH$_3$, —(CH$_2$)$_b$Z or —(CH=CH)$_b$Z when Y=O, and —(CH$_2$)$_a$CH$_3$ when Y=S;

R$^1$ and R$^2$ are each, independently, hydrogen or lower alkyl;

Z is indolyl, furyl, phenyl or phenyl optionally mono- or disubstituted independently by alkyl of 1-7 carbon atoms, haloloweralkyl, perfluoroalkyl, loweralkoxy, aralkoxy, halo or nitro;

a is 0-20 when Y=O, and a is 1-3 when Y=S; and b is 1-2.

The terms "lower alkyl" and "lower alkoxy" refer to moieties having 1 to 6 carbon atoms. The term "aryl" refers to aromatic moieties having 6 to 10 carbon atoms. The term "halo" refers to fluoro, bromo or chloro.

The compounds within the scope of the invention by virtue of their configuration, exhibit stereoisomerism. Accordingly, the compounds of the invention include the diastereomers, enantiomorphs, racemates and mixtures thereof.

The compounds within the scope of the invention can be prepared by a variety of synthetic routes using conventional methods. According to one preparative scheme, a suitable R-containing reactant is condensed with tetronic acid to give an acyl tetronic acid, as exemplified by the condensation of oleic acid and tetronic acid:

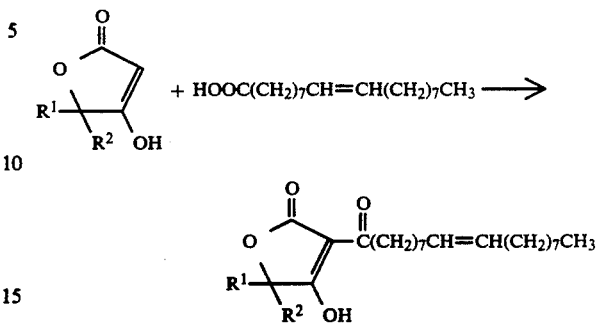

Those compounds of the invention in which R is a moiety of the formula

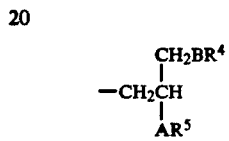

can be prepared by the following procedure. 1-Penten-5-ol is silylated with a suitable silylating agent to yield an intermediate silyloxy diol, which is osmylated to yield a saturated vicinial dihydroxysilyl ether:

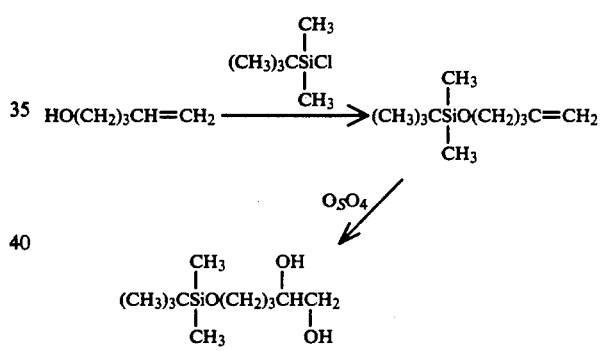

The latter ether can then be condensed, for example, with a suitable alkyl halide in the presence of sodium hydride to yield mono- or bis alkylated intermediates:

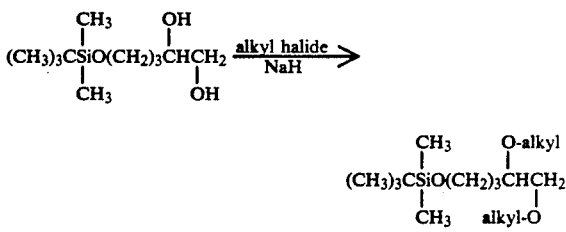

Alternatively, condensation with a carboxylic acid gives a diacylated intermediate, while with an isocyanate, gives a dicarbamoylated intermediate:

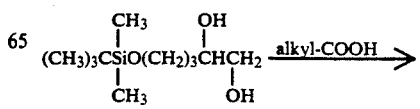

-continued

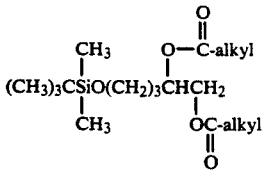

In either case, the resulting intermediate is subjected to deprotection and oxidation to yield, as a reactant, a carboxylic acid, which can then be condensed with tetronic acid to yield the desired final products:

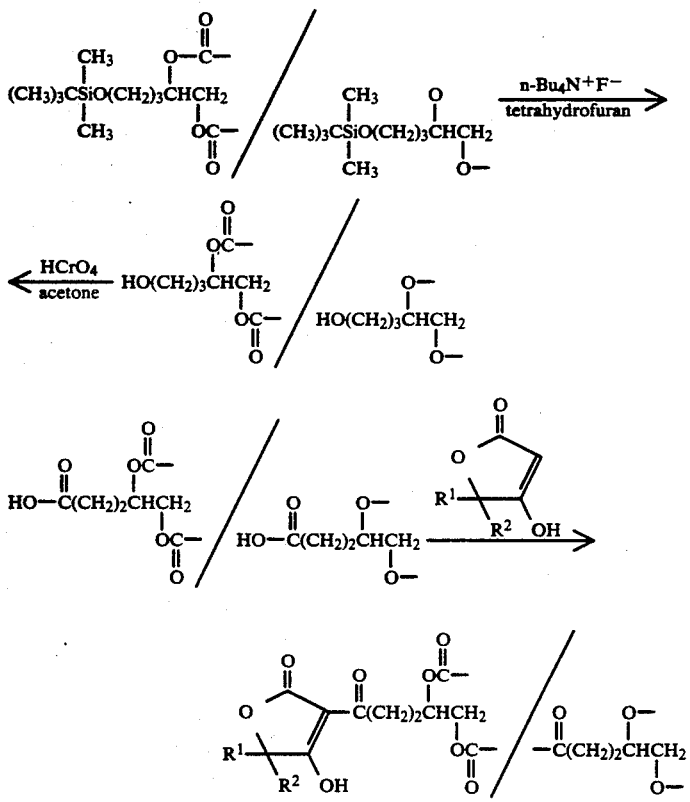

The starting materials in the above preparative sequences are all commercially available or can be prepared by conventional methods as taught in the chemical literature.

The compounds of the invention, by virtue of their ability to inhibit activity of PLA$_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis, psoriasis (and related skin inflammation) and the like.

When the compounds within the scope of the invention are employed in the treatment of allergic airways disorders or in anti-flammatory therapy, they can be formulated into oral dosage forms such as tablets, capsules and the like. The compounds can be administered alone or by combining them with conventional carriers, such as magnesium and carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, inter alia, determine the specificity of action of the compounds of the invention as $PLA_2$ inhibitors as measured by their ability to inhibit the synthesis of $LTB_4$ and $TxB_2$ by rat glycogen -elicited polymorphonuclear leukocytes; their ability to inhibit platelet-activating factor and $LTB_4$ biosynthesis in human neutrophils; as well as measure their ability to inhibit arachidonic acid release mediated by human and non-human source $PLA_2$. The procedures further measure the ability of the compounds of the invention to inhibit, in vivo, the activity of exogenously administered $PLA_2$. The pharmacological testing additionally demonstrates the ability of the compounds of the invention to inhibit, in vivo, the lipoxygenase and cyclooxygenase pathways of arachidonic-acid metabolism; and also measures the in vivo activity of the compounds as anti-inflammatory agents in the rat carrageenan paw edema assay and the murine ear edema assay.

The following examples show the preparation and pharmacological testing of compounds within the invention.

EXAMPLE 1

4-Hydroxy-3-(1-oxodecyl)-2(5H)-furanone

To a solution of 300 mg (3.0 mmol) of tetronic acid and 629 mg (685 μL, 3.3 mmol) of decanoyl chloride is added 527 μL (4.5 mmol) of tin(IV) tetrachloride. The solution is heated in an oil bath at 100° C. for 3 hours. The reaction mixture is worked up by dissolving the cooled black solution in dichloromethane and washing with 1.0N HCl followed by brine. The organic layer is dried over anhydrous sodium sulfate, decanted, and concentrated in vacuo to give a yellow oil. Chromatography on a 2 mm Chromatotron plate eluting with 5% methanol/dichloromethane gives an oil which is crystallized from ethyl acetate to give 119 mg (16%) of product, m.p 71°-74° C.

Spectral data follows. IR (KBr) 1780 (C=O), 1755 (C=O) cm$^{-1}$.

Ms (EI) 254 (M+), 236 (—H$_2$O).

Analysis Calc'd. for $C_{14}H_{22}O_4.0.25\ H_2O$: C, 64.99; H, 8.70; N, 0.00. Found: C, 64.95; H, 8.24; N, 0.18.

EXAMPLE 2

4-Hydroxy-3-(1-oxo-3-phenylpropyl)-2(5H)-furanone

To a solution of 330 mg (3.3 mmole) of tetronic acid, 495 μL (3.63 mmol) of triethylamine, and 132 mg (1.09 mmol) of 4-dimethylaminopyridine in 17 mL of dichloromethane is added at 0° C., 403 μL (3.63 mmol) of hydrocinnamoyl chloride. The iced bath is removed and stirred for 18 hours. The reaction mixture is worked up by pouring into 1.0N HCl and extracting three times with dichloromethane. The organic layers are combined, washed with brine, dried over anhydrous sodium sulfate, decanted, and concentrated in vacuo to give a light yellow solid which is recrystallized from ethyl acetate/hexane to give 363 mg (47%) of product.

Spectral data follows. $^1$H NMR (400 MHz, d$_6$-DMSO) δ 7.11-7.29 (m, 5H, arom), 4.40 (bs, 2H, CH$_2$OC=O), 2.99 (t, 2H, J=6.7 Hz, CH$_2$C=O), 2.77 (t, 2H, J=6.7 Hz, CH$_2$Ph); IR (KBr) 1775 (C=O), 1750 (C=O) cm$^{-1}$; MS (EI) 232 (M+), 214 (—H$_2$O).

Analysis Calc'd. for $C_{13}H_{12}O_4.0.75\ H_2O$: C, 63.54; H, 5.50; N, 0.00. Found: C, 63.83; H, 4.90; N, 0.21

EXAMPLE 3

4-Hydroxy-3-[(phenylmethoxy)acetyl]-2(5H)-furanone

To a solution of 1.0 g (10 mmol) of tetronic acid in 40 mL of dry dichloromethane is added at 0° C., 1.5 mL (11 mmol) of triethylamine and 400 mg (3.3 mmol) of 4-dimethylaminopyridine. Then 2.03 g (1.74 mL, 11 mmol) of benzyloxyacetyl chloride is added dropwise. After 10 minutes, the ice bath is removed. The reaction mixture is stirred overnight at room temperature and is worked up by pouring into 1.0N HCl and extracting three times with ethyl acetate. The organic layers are combined, washed with brine, dried over anhydrous sodium sulfate, decanted, and concentrated in vacuo to give a yellow solid. The solid is recrystallized from ethyl acetate to give 650 mg (26%) of product, m.p. 154°-155° C.

Spectral data follows. $^1$H NMR (400 MHz, CDCl$_3$) δ 7.30-7.42 (m, 5H, arom), 4.73 (s, 2H, OCH$_2$Ph), 4.72 (bs, 2H, CH$_2$OC=O), 4.67 (s, 2H, OCH$_2$C=O); IR (KBr) 1755 (C=O) cm$^{-1}$; MS (EI) no M+ peak, 142 (M-OCH$_2$Ph).

Analysis Calc'd. for $C_{13}H_{12}O_5$: C, 62.90; H, 4.87; N, 0.00. Found: C, 62.44; H, 5.02; N, 0.43.

EXAMPLE 4

4-Hydroxy-3-[3-(1H-indol-3-yl)-1-oxopropyl]-2(5H)-furanone

To a solution of 1.0 g (10 mmol) of tetronic acid in 30 mL of dry dichloromethane is added at 0° C., 1.5 mL (11 mmol) of triethylamine and 400 mg (3.3 mmol) of 4-dimethylaminopyridine. After stirring for 5 minutes, 2.27 g (12 mmol) of 3-(1H-indol-3-yl)propionic acid is added followed by 2.29 g (12 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a brown solid. Trituration with ether gave 2.28 g (84%) of product, m.p. 148°-149° C.

Spectral data follows. $^1$H NMR (400 MHz, d$_6$-acetone) δ 10.02 (bs, 1H, NH), 7.65 (d, 1H, J=7.1 Hz, arom), 7.36 (d, 1H, J=7.1 Hz, arom), 7.20 (s, 1H, arom), 7.09 (t, 1H, J=7.1 Hz, arom), 7.02 (t, 1H, J=7.1 Hz, arom), 4.72 (bs, 2H, CH$_2$OC=O), 3.30 (t, 2H, J=6.5 Hz, CH$_2$C=O), 3.02 (t, 2H, J=6.5 Hz, CH$_2$Ar); IR (KBr) 1750 (C=O) cm$^{-1}$; MS (EI) 271 (M+), 144, 130.

Analysis Calc'd. for $C_{15}H_{13}NO_4.\ 0.25\ H_2O$: C, 65.34; H, 4.90; N, 5.08. Found: C, 65.26; H, 4.89; N, 5.33.

EXAMPLE 5

4-Hydroxy-3-[4-(1H-indol-3-yl)-1-oxobutyl]-2(5H)-furanone

To a solution of 775 mg (7.75 mmol) of tetronic acid in 30 mL of dry dichloromethane is added at 0° C., 1.16 mL (8.53 mmol) of triethylamine and 310 mg (2.58 mmol) of 4-dimethylaminopyridine. After stirring for 5 minutes, 1.89 g (9.3 mmol) of 4-(1H-indol-3-yl)butyric acid is added followed by 1.78 g (9.3 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a brown solid. Trituration with ether gives 1.51 g (68%) of product, m.p 133°–135° C.

Spectral data follows. $^1$H NMR (400 MHz, d$_6$-acetone) δ 9.90 (bs, 1H, NH), 7.52 (d, 1H, J=7.3 Hz, arom), 7.32 (d, 1H, J=7.3 Hz, arom), 7.10 (s, 1H, arom), 6.95 (t, 1H, J=7.3 Hz, arom), 6.93 (t, 1H, J=7.3 Hz, arom), 4.55 (bs, 2H, CH$_2$OC=O), 2.95 (t, 2H, J=6.5 Hz, CH$_2$C=O), 2.85 (t, 2H, J=6.5 Hz, CH$_2$Ar), 2.08 (m, 2H, CH$_2$); IR (KBr) 1760 (C=O) cm$^{-1}$; MS (EI) 285 (M+), 130.

Analysis Calc'd. for C$_{16}$H$_{15}$NO$_4$. 0.25 H$_2$O: C, 66.32; H, 5.35; N, 4.84. Found: C, 66.71; H, 5.73; N, 6.10.

EXAMPLE 6

(E)-4-Hydroxy-3-(3-(4-methoxyphenyl)-1-oxo-2-propenyl)-2 (5H)-furanone

Into a stirring solution of 750 mg (5.27 mmol) of 3-acetyl tetronic acid and 636 mg (4.53 mmol) of p-anisaldehyde in 60 mL of methanol at −10° C. is bubbled HCl gas for 3 hours. The ice bath is removed and HCl is continued for 2 hours at room temperature. The reaction is concentrated in vacuo and the residue is recrystallized from ethanol affording 125 mg (10%) of product.

Spectral data follows. $^1$H NMR (400 MHz, CDCl$_3$) δ 8.01 (d, 0.5H, J=15.9 Hz, olefin), 7.99 (d, 0.5H, J=15.9 Hz, olefin), 7.87 (d, 0.5H, J=25.9 Hz, olefin), 7.80 (d, 0.5H, J=25.9 Hz, olefin), 7.65 (d, 2H, J=8.4 Hz, arom), 7.44 (d, 2H, J=8.4 Hz, arom), 4.66 (s, 2H, OCH$_2$C=O), 3.97 (s, 3H, OCH$_3$); IR (KBr) 3260, 1750 (C=O), 1720 (C=O), 1650, 1570, 1550 cm$^{-1}$.

Analysis Calc'd. for C$_{14}$H$_{12}$O$_5$: C, 64.61; H, 4.61; N, 0.00. Found: C, 64.52; H, 4.42; N, 0.00.

EXAMPLE 7

(E)-4-Hydroxy-3-(3-(4-chlorophenyl)-1-oxo-2-propenyl)-2(5H)-furanone

Into a stirring solution of 750 mg (5.27 mmol) of 3-acetyl tetronic acid and 636 mg (4.53 mmol) of p-chlorobenzaldehyde in 60 mL of methanol at −10° C. is bubbled HCl gas for 3 hours. The ice bath is removed and HCl gas is continued for 2 hours. The reaction is concentrated in vacuo and the residue is recrystallized from ethanol affording 523 mg (44%) of product, m.p 158° C.

Spectral data follows. $^1$H NMR (400 MHz, CDCl$_3$) δ 8.00 (d, 0.5H, J=16.0 Hz, olefin) 7.98 (d, 0.5H, J=16.0 Hz, olefin), 7.77 (d, 0.5H, J=26.0 Hz, olefin), 7.70 (d, 0.5H, J=26.0 Hz, olefin), 7.64 (d, 2H, J=8.3 Hz, arom), 7.44 (d, 2H, J=8.3 Hz, arom), 4.67 (s, 1H, OCH$_2$C=O), 4.61 (s, 1H, OCH$_2$C=O), 3.10 (bs, 1H, OH); IR (KBr) 3160, 1750 (C=O), 1700 (C=O), 1640, 1580, 1570 cm$^{-1}$; MS (EI) 266 (M+), 264 (100), 246, 165, 137.

Analysis Calc'd. for C$_{13}$H$_9$O$_4$Cl: C, 59.00; H, 3.34; N, 0.00. Found: C, 58.57; H, 3.57; N, 0.00.

EXAMPLE 8

(E)-4-Hydroxy-3-(3-(phenyl)-1-oxo-2-propenyl)-2(5H)-furanone

Into a stirring solution of 500 mg (3.52 mmol) of 3-acetyl tetronic acid and 308 μL (3.03 mmol) of benzaldehyde in 60 mL of methanol at −10° C. is bubbled HCl gas for 3 hours. The ice bath is removed and HCl is continued for 2 hours. The reaction is concentrated in vacuo and the residue is recrystallized from ethanol affording 387 mg (56%) of product, m.p 136°–138° C.

Spectral data follows. $^1$H NMR (400 MHz, CDCl$_3$) δ 8.07 (d, 0.5H, J=16.0 Hz, olefin) 8.05 (d, 0.5H, J=16.0 Hz, olefin), 7.81 (d, 0.5H, J=28.1 Hz, olefin), 7.77 (d, 0.5H, J=28.1 Hz, olefin), 7.71–7.72 (m, 2H, arom), 7.43–7.51 (m, 3H, arom), 4.67 (s, 1H, OCH$_2$C=O), 4.60 (s, 1H, OCH$_2$C=O); IR (KBr) 3400, 1765 (C=O), 1755 (C=O); 1650 (C=O), 1620, 1575, 1560 cm$^{-1}$; MS (EI) 230 (M+), 149 (100).

Analysis Calc'd. for C$_{13}$H$_{10}$O$_4$: C, 67.82; H, 4.38; N, 0.00. Found: C, 67.49; H, 4.49; N, 0.00.

EXAMPLE 9

(Z)-4-Hydroxy-3-(1-oxo-9-octadecenyl)-2(5H)-furanone

To a solution of 1.48 g (14.75 mmol) of tetronic acid in 45 mL of dry dichloromethane is added at 0° C., 2.22 mL (16.22 mmol) of triethylamine and 592 mg (4.92 mmol) of 4-dimethylaminopyridine. After stirring for 5 minutes, 5.0 g (17.7 mmol) of oleic acid is added followed by 3.38 g (17.7 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a light yellow solid. Trituration with cold pentane gives 3.85 g (72%) of product, 46°–48° C.

Spectral data follows. $^1$H NMR (400 MHz, d$_6$-DMSO) δ 5.30 (m, 2H, olefin), 4.53 (bs, 2H, CH$_2$OC=O), 2.63 (t, 2H, J=6.0 Hz, CH$_2$C=O), 1.96 (m, 4H, CH$_2$C=C), 1.55–1.05 (m, 22H, CH$_2$), 0.83 (t, 3H, J=6.0 Hz, CH$_3$); IR (KBr) 1740 (C=O); MS (CI) 365 (M+1), 143, 171.

Analysis Calc'd. for C$_{22}$H$_{36}$O$_4$: C, 72.53; H, 9.89; N, 0.00. Found: C, 72.99; H, 10.12; N, 0.06.

EXAMPLE 10

(E)-4-Hydroxy-3-(1-oxo-3-(3-(trifluoromethyl)phenyl)-2-propenyl)-2 (5H)-furanone Into a stirring solution of 750 mg (5.27 mmol) of 3-acetyl tetronic acid and 606 μL (4.53 mmol) of m-trifluoromethylbenzaldehyde in 60 mL of methanol at −10° C. is bubbled HCl gas for 3 hours. The ice bath is removed and HCl is continued for 2 hours. The reaction is concentrated in vacuo and the residue is recrystallized from ethanol affording 263 mg (20%) of product, m.p 171°–175° C.

Spectral data follows. $^1$H NMR (400 MHz, d$_6$-DMSO) δ 8.02 (d, 1H, J=16.1 Hz, olefin), 7.95 (m, 2H, arom), 7.75 (m, 1H, arom) 7.66 (m, 1H, arom), 7.64 (d, 1H, J=16.1 Hz, olefin), 4.37 (s, 2H, OCH$_2$C=O); IR (KBr) 3400, 1730 (C=O), 1705 (C=O), 1690 (C=O), 1630, 1600, 1555 cm$^{-1}$; MS (EI) 298 (M+), 271, 239, 238, 199 (100), 151, 115.

Analysis Calc'd. for C$_{14}$H$_9$F$_3$O$_4$: C, 56.42; H, 3.04; N, 0.00. Found: C, 56.08; H, 2.99; N, 0.00.

EXAMPLE 11

4-Hydroxy-3-(1-oxoeicosanoyl)-2(5H)-furanone

To a stirring suspension of 8.76 g (87.6 mmol) of tetronic acid in 200 mL of dichloromethane at 0° C. is added 13.4 mL (96.4 mmol) of triethylamine and 3.5 g (31.0 mmol) of 4-dimethylaminopyridine. After allowing the reaction mixture to stir for 5 minutes, 17 g (96.4 mmol) of eicosanoic acid and 20 g (105.0 mmol) of 1-(3-dimethylaminopropyl)-3-ethylcarbodiimide hydrochloride are added. The reaction mixture is allowed to stir at room temperature for 48 hours. Then, 100 mL of water is added to the reaction and the layers are separated. The aqueous layer is extracted three times with 50 mL of dichloromethane. The aqueous layer is acidified with 100 mL of 1.0N HCl and extracted three times with 100 mL of dichloromethane. The combined organic layers are dried over anhydrous sodium sulfate and concentrated in vacuo. The residue is triturated in ethyl ether and filtered, affording 14.3 g (64%) of product, m.p 91°-92° C.

Spectral data follows. $^1$H NMR (400 MHz, CDCl$_3$) $\delta$ 4.63 (bs, 2H, OCH$_2$C=O), 2.92 (t, 2H, J=7.6 Hz, CH$_2$C=O), 1.70 (m, 2H, CH2CH$_2$C=O), 1.27-1.41 (m, 12H, CH$_2$), 0.88 (t, 3H, J=6.9 Hz, CH$_2$CH$_3$); IR (KBr) 3200, 2900, 2850, 1780 (C=O), 1750 (C=O), 1660, 1650, 1615 cm$^{-1}$; MS (EI) 255 (M+), 254, 236, 155, 142 (100), 127.

Analysis Calc'd. for C$_{14}$H$_{22}$O$_4$: C, 66.12; H, 8.72; N, 0.00. Found: C, 66.26; H, 8.59; N, 0.00.

EXAMPLE 12

(E)-4-Hydroxy-3-(3-(3-nitrophenyl)-1-oxo-2-propenyl)-2(5H)-furanone

Into a stirring solution of 750 mg (5.27 mmol) of 3-acetyl tetronic acid and 686 mg (4.53 mmol) of 3-nitrobenzaldehyde in 60 mL of methanol at −10° C. is bubbled HCl gas for 3 hours. The ice bath is removed and HCl is continued for 2 hours. The reaction is concentrated in vacuo and the residue is recrystallized from ethanol affording 210 mg (17%) of product, m.p 168°-170° C.

Spectral data follows. $^1$H NMR (400 MHz, CDCl$_3$) $\delta$ 8.49 (m, 1H, arom), 8.33 (m, 1H, arom), 8.05 (m, 2H, arom), 7.89 (d, 0.5H, J=18.5 Hz, olefin), 7.85 (d, 0.5H, J=18.5 Hz, olefin), 7.67 (t, 1H, J=8.0, arom), 4.71 (s, 1H, OCH$_2$C=O), 4.64 (s, 1H, OCH$_2$C=O); IR (KBr) 3400, 1755 (C=O), 1700 (C=O), 1630, 1610, 1580, 1560, 1530 cm$^{-1}$; MS (EI) 275 (M+), 176, 69 (100).

Analysis Calc'd. for C$_{13}$H$_9$NO$_6$: C, 56.73; H, 3.30; N, 5.09. Found: C, 56.28; H, 3.11; N, 4.96.

EXAMPLE 13

(E)-3-(3-(2,5-Dimethoxyphenyl)-1-oxo-2-propenyl)-4-hydroxy-2(5H)-furanone

Into a stirring solution of 750 mg (5.27 mmol) of 3-acetyl tetronic acid and 753 mg (4.53 mmol) of 2,5-dimethoxybenzaldehyde in 60 mL of methanol at −10° C. is bubbled HCl gas for 3 hours. The ice bath is removed and HCl is continued for 2 hours. The reaction is concentrated in vacuo and the residue is recrystallized from ethanol, affording 60 mg (4.5%) of product, m.p. 169°-171° C.

Spectral data follows. $^1$H NMR (400 MHz, CDCl$_3$) $\delta$ 8.04 (d, 0.5H, J=10.0 Hz, olefin), 8.00 (d, 0.5H, J=10.0 Hz, olefin), 7.67 (d, 0.5H, J=15.8 Hz, olefin), 7.58 (d, 0.5H, J=15.8 Hz, olefin), 7.32 (m, 1H, arom), 7.20 (m, 1H, arom), 6.94 (m, 1H, arom), 4.65 (s, 1H, OCH$_2$-C=O), 4.59 (s, 1H, OCH$_2$C=O), 3.97 (s, 6H, OCH$_3$); IR (KBr) 3450, 1765 (C=O), 1690 (C=O), 1625, 1580, 1560, 1550, 1510 cm$^{-1}$; MS (EI) 290 (M+), 137, 69 (100).

Analysis Calc'd. for C$_{15}$H$_{14}$O$_6$: C, 62.07; H, 4.86; N, 0.00. Found: C, 62.00; H, 4.87; N, 0.00.

EXAMPLE 14

(Z,Z)-4-Hydroxy-3-(1-oxo-9,12-octadecadienyl)-2(5H)-furanone

To a solution of 1.48 g (14.75 mmol) of tetronic acid in 45 mL of dry dichloromethane is added at 0° C., 2.22 mL (16.22 mmol) of triethylamine and 592 mg (4.92 mmol) of 4-dimethylaminopyridine. After stirring for 5 minutes, 4.96 g (17.7 mmol) of linoleic acid is added, followed by 3.38 g (17.7 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0 N HCl and extracted three times with ethyl acetate. The organic layers are combined, washed with brine, dried over anhydrous sodium sulfate, decanted, and concentrated in vacuo to give a light waxy yellow solid. Trituration with cold pentane gives 4.54 g (85%) of product.

Spectral data follows. $^1$H NMR (400 MHz, CDCl$_3$) $\delta$ 5.40 (m, 4H, olefin), 4.64 (bs, 2H, CH$_2$OC=O), 2.93 (t, 2H, J=6.4 Hz, CH$_2$C=O), 2.78 (m, 2H, C=CCH$_2$C=C), 2.06 (m, 4H, CH$_2$C=C), 1.71-1.36 (m, 16H, CH$_2$), 0.92 (t, 3H, J=6.5 Hz, CH$_3$); IR (KBr) 1775 (C=O) cm$^{-1}$; MS (FAB) 363 (M+H).

Analysis Calc'd. for C$_{22}$H$_{34}$O$_4$.0.25 H$_2$O: C, 72.03; H, 9.41; N, 0.00. Found: C, 71.93; H, 9.65; N, 0.00.

EXAMPLE 15

(Z,Z,Z)-4-Hydroxy-3-(1-oxo-9,12,15-octadecatrienyl)-2(5H)-furanone

To a solution of 1.48 g (14.75 mmol) of tetronic acid in 45 mL of dry dichloromethane is added at 0° C., 2.22 mL (16.22 mmol) of triethylamine and 592 mg (4.92 mmol) of 4-dimethylaminopyridine. After stirring for 5 minutes, 4.92 g (17.7 mmol) of linolenic acid is added, followed by 3.38 g (17.7 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a light brown waxy solid. Trituration with cold pentane gives 4.38 g (83%) of product.

Spectral data follows. $^1$H NMR (400 MHz, CDCl$_3$) $\delta$ 5.39 (m, 6H, olefin), 4.61 (bs, 2H, CH$_2$OC=O), 2.90 (t, 2H, J=7.0 Hz, CH$_2$C=O), 2.79 (m, 4H, C=CCH$_2$C=C), 2.08 (m, 4H, CH$_2$C=C), 1.68-1.34 (m, 10H, CH$_2$), 0.99 (t, 3H, J=6.5 Hz, CH$_3$); IR (KBr) 1775 (C=O) cm$^{-1}$; MS (FAB) 361 (M+H).

Analysis Calc'd. for C$_{22}$H$_{34}$O$_4$. H$_2$O: C, 69.84; H, 8.99; N, 0.00. Found: C, 69.68; H, 8.72; N 0.00.

EXAMPLE 16

(E)-3-(3-(3,4-Dimethoxyphenyl)-1-oxo-2-propenyl)-4-hydroxy-2 (5H)-furanone

Into a stirring solution of 750 mg (5.27 mmol) of 3-acetyl tetronic acid and 753 mg (4.53 mmol) of 3,4-dimethoxybenzaldehyde in 60 mL of methanol at −10° C. is bubbled HCl gas for 3 hours. The ice bath is removed and HCl is continued for 2 hours. The reaction is concentrated in vacuo and the residue is recrystallized from ethanol affording 135 mg (10%) of product, m.p. 191°-192° C.

Spectral data follows. $^1$H NMR (400 MHz, CDCl$_3$) δ 7.83 (d, 1H, J=15.9 Hz, olefin), 7.64 (d, 1H, J=15.9 Hz, olefin), 7.34 (d of d, 1H, J$_1$=1.9 Hz, J$_2$=8.5 Hz, arom), 7.28 (d, 1H, J=1.9 Hz, arom), 7.07 (d, 1H, J=8.5 Hz, arom), 4.59 (s, 2H, OCH$_2$C=O), 3.81 (s, 3H, OCH$_3$); IR (KBr) 3450, 2940, 2840, 1760 (C=O), 1685 (C=O), 1630, 1580, 1555, 1505 cm$^{-1}$; MS (EI) 291 (M+), 202, 85, 81, 71, 69 (100), 67.

Analysis Calc'd. for C$_{15}$H$_{14}$O$_6$: C, 62.07; H, 4.86; N, 0.00. Found: C, 61.70; H, 4.87; N, 0.00.

EXAMPLE 17

(Z)-4-Hydroxy-5,5-dimethyl-3-(1-oxo-9-octadecenyl)-2(5H)-furanone

To a solution of 1.89 g (14.75 mmol) of 5,5-dimethyltetronic acid in 45 mL of dry dimethylformamide is added at 0° C., 2.22 mL (16.22 mmol) of triethylamine and 592 mg (4.92 mmol) of 4-dimethylaminopyridine. After stirring for 5 minutes, 5.00 g (17.7 mmol) of oleic acid is added followed by 3.38 g (17.7 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0 N HCl and extracted three times with ethyl acetate. The organic layers are combined, washed with brine, dried over anhydrous sodium sulfate, decanted, and concentrated in vacuo to give a light yellow oil. Trituration with cold pentane gives 4.38 g (83%) of product.

Spectral data follows. $^1$H NMR (400 MHz, d$_6$-DMSO) δ 5.30 (m, 2H, olefin), 2.69 (t, 2H, J=6.5 Hz, CH$_2$C=O), 1.97 (m, 4H, CH$_2$C=C), 1.43-1.22 (m, 22H, CH$_2$), 0.83 (t, 3H, J=6.5 Hz, CH$_3$); IR (KBr) 1770 (C=O) cm$^{-1}$; MS (EI) 392 (M+), 374, 183.

Analysis Calc'd. for C$_{22}$H$_{34}$O$_4$.1.5 H$_2$O: C, 68.74; H, 10.26; N, 0.00. Found: C, 68.90; H, 9.44; N, 0.24.

EXAMPLE 18

(Z)-4-Hydroxy-3-(1-oxo-6-octadecenyl)-2(5H)-furanone

To a solution of 1.48 g (14.75 mmol) of tetronic acid in 45 mL of dry dimethylformamide is added at 0° C., 2.22 mL (16.22 mmol) of triethylamine and 592 mg (4.92 mmol) of 4-dimethylaminopyridine. After stirring for 5 minutes, 5.00 g (17.7 mmol) of petroselenic acid is added, followed by 3.38 g (17.7 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a light yellow solid. Recrystallization from cold pentane gives 3.20 g (28%) of product, m.p 41°-42° C.

Spectral data follows. $^1$H NMR (400 MHz, CDCl$_3$) δ 5.35 (m, 2H, olefin), 4.58 (bs, 2H, CH$_2$OC=O), 2.72 (t, 2H, J=6.5 Hz, CH$_2$C=O), 1.98 (m, 4H, CH$_2$C=C), 1.58-1.20 (m, 22H, CH$_2$), 0.84 (t, 3H, J=6.5 Hz, CH$_3$); IR (KBr) 1775 (C=O), 1750 (C=O) cm$^{-1}$; MS (EI) 364 (M+).

Analysis Calc'd. for C$_{22}$H$_{36}$O$_4$: C, 72.49; H, 9.95; N, 0.00. Found: C, 72.05; H, 9.93; N, 0.02.

EXAMPLE 19

(Z)-4-Hydroxy-3-(1-oxo-8-(2'-octylcyclopropyl)octanyl)-2(5H)-furanone

To a solution of 1.48 g (14.75 mmol) of tetronic acid in 45 mL of dry dimethylformamide is added at 0° C., 2.22 mL (16.22 mmol) of triethylamine and 592 mg (4.92 mmol) of 4-dimethylaminopyridine. After stirring for 5 minutes, 5.25 g (17.7 mmol) of cis-8-(2'-octylcyclopropyl)octanoic acid is added followed by 3.38 g (17.7 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a colorless solid. Recrystallization from cold pentane gave 3.20 g (57%) of product, m.p 49°-50° C.

Spectral data follows. $^1$H NMR (400 MHz, CDCl$_3$) δ 4.62 (bs, 2H, CH$_2$OC=O), 2.95 (t, 2H, J=6.0 Hz, CH$_2$C=O), 1.71 (m, 2H, CH$_2$), 1.45-1.20 (m, 22H, CH$_2$), 1.15 (m, 2H, cyclopropyl CH$_2$), 0.92 (t, 3H, J=6.5 Hz, CH$_3$), 0.90-0.70 (m, 1.5H, cyclopropyl CH$_2$), −0.35 (m, 0.5H, cyclopropyl CH$_2$); IR (KBr) 1775 (C=O), 1760 (C=O) cm$^{-1}$.

Analysis Calc'd. for C$_{23}$H$_{38}$O$_4$: C, 72.98; H, 10.12; N, 0.00. Found: C, 72.52; H, 9.94; N, 0.05.

EXAMPLE 20

(Z,Z,Z)-4-Hydroxy-3-(1-oxo-6,9,12-octadecatrienyl)-2(5H)-furanone

To a solution of 300 g (2.98 mmol) of tetronic acid in 10 mL of dry dimethylformamide is added at 0° C., 450 μL (3.29 mmol) of triethylamine and 121 mg (1.0 mmol) of 4-dimethylaminopyridine. After stirring for 5 minutes, 1.00 g (3.59 mmol) of gamma-linolenic acid is added followed by 668 mg (3.59 mmol) of 1-(3-dimethylaminopropyl)-3-ethylcarbodiimide hydrochloride. After 10 minutes, the ice bath is removed. The reaction mixture is stirred at room temperature overnight. The reaction mixture is poured into 1.0N HCl and extracted three times with ethyl acetate. The organic layers are combined, washed with brine, dried over anhydrous sodium sulfate, decanted, and concentrated in vacuo to give a brown oil. Flash chromatography on a 40 mm × 150 mm silica column eluting with 5% methanol-ethyl acetate gives 150 mg (14%) of product.

Spectral data follows. $^1$H NMR (400 MHz, CDCl$_3$) δ 5.41 (m, 6H, olefin), 4.62 (bs, 2H, CH$_2$OC=O), 2.94 (t, 2H, J=7.0 Hz, CH$_2$C=O), 2.80 (m, 4H, C=CCH$_2$C=C), 2.09 (m, 4CH$_2$C=C), 1.75-1.24 (m, 10H, CH$_2$), 0.90 (t, 3H, J=6.5 Hz, CH$_3$); IR (KBr) 1770 (C=O) cm$^{-1}$; MS (EI) 360 (M+).

EXAMPLE 21

4-Hydroxy-3-[6-(4-chlorophenoxy)-1-oxohexyl]-2(5H)-furanone

To a stirring solution of 554 mg (5.54 mmol) of tetronic acid in 20 mL of diemthylformamide is added 850 μL (6.09 mmol) of triethylamine and 220 mg (1.765 mmol) of 4-dimethylaminopyridine at 0° C. Next, 1.26 g (6.63 mmol) of 1-(3-dimethylaminopropyl)-3-ethylcarbodiimide hydrochloride and 1.475 g (6.63 mmol) of 6-[4-(hexyloxy)phenoxy]hexanoic acid are added and the reaction mixture is stirred 2 days at room temperature. The reaction is acidified with 1.0N HCl and extracted three times with ether. The combined organic layers are dried over MgSO4 and concentrated in vacuo giving a yellow solid. Pure material is obtained by trituration in ether, filtering to give 774 mg (43%) of 4-hydroxy-3-[6-(4-chlorophenoxy)-1-oxohexyl]-2(5H)-furanone.

Spectral data follows: $^1$H NMR (CDCl$_3$, 400 MHz) δ 7.216 (d, 2H, Ar), 6.818 (d, 2H, Ar), 4.681 (s, 2H, CH$_2$OC=O), 3.930 (t, 2H, CH$_2$OAr), 2.954 (t, 2H, O=CCH$_2$), 1.836–1.559 (m, 6H, CH$_2$); IR (KBr) 3200, 2980, 2920, 2860, 1775, 1750, 1660, 1620, 1490, 1245, 1050 cm$^{-1}$; MS (EI) 324 (M+), 197, 142, 128 (100), 127.

Analysis Calc'd. for C$_{16}$H$_{17}$O$_5$Cl.0.25H$_2$O: C, 58.36; H, 5.36. Found: C, 58.78; H, 5.20.

EXAMPLE 22

4-Hydroxy-3-[1-oxo-8-[2-[(2-pentylcyclopropyl)methyl]cyclopropyl]octyl]-2(5H)-furanone To a stirring solution of 947 mg (9.5 mmol) of tetronic acid in 30 mL of dimethylformamide is added 1.42 mL (10.45 mmol) of triethylamine and 379 mg (3.14 mmol) of 4-dimethylaminopyridine at 0° C. Next, 2.17 g (11.4 mmol) of 1-(3-dimethylaminopropyl)-3-ethylcarbodiimide hydrochloride and 3.5 g (11.4 mmol) of (cis)-7-(2-octylcyclopropyl)octanoic acid are added and the reaction mixture is stirred 2 days at room temperature. The reaction is acidified with 1.0N HCl and extracted three times with ethyl acetate. The combined organic layers are dried over Na$_2$SO$_4$ and concentrated in vacuo giving a yellow oil. Pure material is obtained by flash chromatography on a 40 mm × 150 mm silica column eluting with 50% ethyl acetate/hexane to 100% ethyl acetate giving 870 mg (20%) of 4-hydroxy-3-[1-oxo-8-[2-[(2-pentylcyclopropyl)methyl]cyclopropyl]octyl]-2(5H)-furanone as an oil.

Spectral data follows: $^1$H NMR (CDCl$_3$, 400 MHz) δ 4.572 (s, 2H, CH$_2$OC=O), 2.704 (t, 2H, O=CCH$_2$), 1.481 (m, 2H, O=CCH$_2$CH$_2$), 1.341–1.111 (m, 20H, CH$_2$), 0.845 (t, 3H, CH$_2$CH$_3$), 0.747–0.644 (m, 4H, cyclopropyl), 0.559 (m, 2H, cyclopropyl), −0.332 (m, 2H, cyclopropyl); IR (KBr) 3060, 2990, 2910, 2840, 1770, 1695, 1655, 1600, 1455, 1435, 1195, 1040 cm$^{-1}$; MS (EI) 390 (M+), 127 (100), 67(94).

Analysis Calc'd. for C$_{24}$H$_{38}$O$_4$: C, 73.81; H, 9.81. Found: C, 73.59; H, 9.83.

EXAMPLE 23

4-Hydroxy-3-((Z)-1-oxo-10-tetradecenyl)-2(5H)-furanone

To a stirring solution of 523 mg (5.22 mmol) of tetronic acid in 17 mL of dimethylformamide is added 800 μL (5.75 mmol) of triethylamine and 210 mg of 4-dimethylaminopyridine at 0° C. Next, 1.19 g (5.75 mmol) of 1-(3-dimethylaminopropyl)-3-ethylcarbodiimide hydrochloride and 1.2 g (5.75 mmol) of (Z)-10-tetradecenoic acid are added and the reaction mixture is stirred overnight at room temperature. The reaction is acidified with 1.0N HCl and extracted with four 50 mL portions of ether. The combined organic layers are dried over MgSO$_4$ and concentrated in vacuo affording crude compound. Pure material is obtained by flash chromatography with 10% methanol/ethyl acetate as eluant affording 1.2 g (75%) of 4-hydroxy-3-((Z)-1-oxo-10-tetradecyl)-2(5H)-furanone.

Spectral data follows: $^1$H NMR (d$_6$-DMSO, 400 MHz) δ 5.356 (m, 2H, HC=CH), 4.509 (s, 2H, CH$_2$OC=O), 2.686 (t, 2H, O=CCH$_2$), 1.932 (m, 4H, CH$_2$C=CCH$_2$), 1.470 (m, 2H, O=CCH$_2$CH$_2$), 1.225 (s, 12H, CH$_2$), 0.851 (t, 3H,CH$_2$CH$_3$); IR (KBr) 2900, 2820, 1770, 1745, 1690, 1650, 1610, 1455, 1435, 1385, 1340, 1305, 1275, 1235, 1230, 1125,1060, 1015 cm$^{-1}$; MS (EI) 310, 308 (M+.), 290,155, 142 (100), 127.

Analysis Calc'd. for C$_{18}$H$_{28}$O$_4$: C, 70.10; H, 9.15. Found: C, 69.89; H, 9.43.

EXAMPLE 24

(Z)-9-Octadecanoic acid 5-(2,5-dihydro-4-hydroxy-3-furanyl)-5-oxo-1,2-pentanediyl ester A. 4,5-Bis[((Z)-1-oxo-9-octadecenyl)oxy]pentanoic acid To a stirring solution of 3.76 g (16.1 mmol) of (Z)-5-[[(1,1-dimethylethyl)dimethylsilyl]oxy]-1-pentene-1,2-diol in 50 mL of methylene chloride is added 4.9 mL (35.2 mmol) of triethylamine and 1.3 g of 4-dimethylaminopyridine at 0° C. Next, 7.4 g (38.6 mmol) of 1-(3-dimethylaminopropyl)-3-ethylcarbodiimide hydrochloride and 10 g (35.4 mmol) of oleic acid are added and the reaction mixture is stirred overnight at room temperature. The reaction is poured into water and extracted with four 50 mL portions of methylene chloride. The combined organic layers are dried over MgSO$_4$ and concentrated in vacuo. The resulting crude diester dissolved in 32 mL of tetrahydrofuran and treated with 32 mL (32 mmol) of 1.0 N tetrabutylammonium fluoride in tetrahydrofuran and the reaction is stirred 2 hours at room temperature. The reaction is poured into water and extracted with four 50 mL portions of ether. The combined organic layers are dried over MgSO$_4$ and concentrated in vacuo affording crude compound. Pure material was obtained by flash chromatography with 15% ethyl acetate/hexane as eluant giving 7.7 g (77%) of alcohol. Next, 20 mL of 2.0M Jones reagent is added at 0° C. to a stirring solution of 7.7 g (11.86 mmol) of the alcohol and the reaction is stirred for 2 hours. The reaction is poured into water and extracted with four 50 ml portions of ether. The combined organic layers are dried over MgSO$_4$ and concentrated in vacuo affording crude compound. Pure material was obtained by flash chromatography with 35% ethyl acetate/hexane as eluant giving 2.2 g (28%) of 4,5-bis[((Z)-1-oxo-9-octadecyl)oxy]pentanoic acid.

Spectral data follows: $^1$H NMR (CDCl$_3$, 400 MHz) δ 5.344 (m, 4H, HC=CH), 5.175 (m, 1H, HCOC=O), 4.145 (m, 2H, H$_2$COC=O), 2.422 (t, 2H, HO$_2$CCH$_2$), 2.301 (t, 4H, O(C=O)CH$_2$), 2.012 (m, 8H, C=CCH$_2$), 1.612 (m, 4H, O(C=O)CH$_2$CH$_2$), 1.289 (m, 40H, CH$_2$), 0.881 (t, 6H, CH$_2$CH$_3$); IR (KBr) 3000, 2920, 2840, 1740,1710,1460, 1160 cm$^{-1}$; MS (CI+) 664 (MH++), 663 (MH+), 645, 381 (100), 338, 265, 159, 87.

Analysis Calc'd. for $C_{41}H_{74}O_6$: C, 74.27; H, 11.25. Found: C, 73.92; H, 11.28.

B) (Z)-9-Octadecanoic acid 5-(2,5-dihydro-4-hydroxy-3-furanyl)-5-oxo-1,2-pentanediyl ester To a stirring solution of 137 mg (1.37 mmol) of tetronic acid in 10 mL of dimethylformamide are added 220 µL (1.5 mmol) of triethylamine and 70 mg of 4-dimethylaminopyridine at 0° C. Next, 330 mg (1.72 mmol) of 1-(3-dimethylaminopropyl)-3-ethylcarbodiimide hydrochloride and 1.0 g (1.5 mmol) of 4,5-bis[((Z)-1-oxo-9-octadecenyl)oxy]pentanoic acid and the reaction is stirred overnight at room temperature. The reaction is acidified with 1.0N HCl and extracted with four 50 mL portions of ether. The combined organic layers are dried over $MgSO_4$ and concentrated in vacuo affording crude compound. Pure material was obtained by flash chromatography with 10% methanol/ethyl acetate as eluant affording 608 mg (60%) of (Z)-9-octadecanoic acid 5-(2,5-dihydro-4-hydroxy-3-furanyl)-5-oxo-1,2-pentanediyl ester.

Spectral data follows: $^1H$ NMR ($d_6$-DMSO, 400 MHz) δ 6.68 (bs, 1H, OH), 5.290 (m, 4H, HC=CH), 4.980 (s, 1H, HCOC=O), 4.500 (s, 2H, $CH_2OC=O$), 4.216 (s, 1H, $CH_2OC=O$), 3.974 (s, 1H, $CH_2OC=O$), 2.726 (m, 2H, O=$CCH_2$), 2.218 (s, 4H, O=$CCH_2$), 1.953 (m, 8H, C=$CCH_2$), 1.477 (s, 4H, O=$CCH_2CH_2$), 1.220 (s, 40H, $CH_2$), 0.830 (t, 6H, $CH_2CH_3$); IR (KBr) 3000, 2900, 2840, 1760, 1730, 1690, 1650, 1600, 1460, 1450, 1430, 1220, 1165, 1035, 1010 cm$^{-1}$; MS (CI+) 463, 409 (100), 265, 69.

Analysis Calc'd. for $C_{45}H_{76}O_8$: C, 72.54; H, 10.28. Found: C, 72.58; H, 10.48.

EXAMPLE 25

4-Hydroxy-3-((Z)-1-oxo-9-tetradecenyl)-2(5H)-furanone

To a stirring solution of 111 mg (1.11 mmol) of tetronic acid in 5 mL of dimethylformamide is added 185 µL (1.33 mmol) of triethylamine and 100 mg of 4-dimethylaminopyridine at 0° C. Next, 303 mg (1.33 mmol) of 1-(3-dimethylaminopropyl)-3-ethylcarbodiimide hydrochloride and 300 mg (1.33 mmol) of myristoleic acid are added and the reaction mixture is stirred 3 days at room temperature. The reaction is acidified with 1.0N HCl and extracted with four 100 mL portions of ethyl acetate. The combined organic layers are dried over $MgSO_4$ and concentrated in vacuo affording crude compound. Pure material is obtained by flash chromatography with 10% methanol/ethyl acetate as eluant affording 280 mg (82%) of 4-hydroxy-3-((Z)-1-oxo-9-tetradecenyl)-2(5H)-furanone.

Spectral data follows: $^1H$ NMR ($CDCl_3$, 400 MHz) δ 5.349 (m, 2H, HC=CH), 4.615 (s, 2H, $CH_2OC=O$), 2.919 (t, 2H, O=$CCH_2$), 2.010 (m, 4H, $CH_2C=CCH_2$), 1.704 (m, 2H, O=$CCH_2CH_2$), 1.314 (m, 12H, $CH_2$), 0.896 (t, 3H, $CH_2CH_3$); IR (KBr) 3200, 3000, 2930, 2860, 1775, 1750, 1660, 1615, 1960, 1435, 1390, 1345, 1275, 1235, 1125, 1060, 1015 cm$^{-1}$; MS (EI) 308 (M+.), 290, 155, 142 (100), 127, 69, 67.

Analysis Calc'd. for $C_{18}H_{28}O_4$: C, 70.10; H, 9.15. Found: C, 70.01; H, 9.50.

EXAMPLE 26

4-Hydroxy-3-((Z)-1-oxo-9-hexadecenyl)-2(5H)-furanone

To a stirring solution of 1.07 g (10.72 mmol) of tetronic acid in 30 mL of dimethylformamide is added 1.64 mL (11.97 mmol) of triethylamine and 428 mg of 4-dimethylaminopyridine at 0° C. Next, 2.44 g (12.77 mmol) of 1-(3-dimethylaminopropyl)-3-ethylcarbodiimide hydrochloride and 3.0 g (11.79 mmol) of palmitoleic acid are added and the reaction is stirred for 3 days at room temperature. The reaction is acidified with 1.0N HCl and extracted with four 100 mL portions of ethyl acetate. The combined organic layers are dried over $MgSO_4$ and concentrated in vacuo affording crude compound. Pure material was obtained by flash chromatography with 10% methanol/ethyl acetate as eluant affording 1.3 g (36%) of 4-hydroxy-3-((Z)-1-oxo-9-hexadecenyl)-2(5H)-furanone.

Spectral data follows: $^1H$ NMR ($CDCl_3$, 400 MHz) δ 5.343 (m, 2H, HC=CH), 4.615 (d, 2H, $CH_2OC=O$), 2.918 (t, 2H, O=$CCH_2$), 2.019 (m, 4H, C=$CCH_2$), 1.704 (m, 2H, O=$CCH_2CH_2$), 1.312 (m, 16H, $CH_2$), 0.883 (t, 3H, $CH_2CH_3$); IR (KBr) 3200, 3000, 2920, 2850, 1775, 1750, 1660, 1615, 1460, 1440, 1390, 1345, 1305, 1275, 1235, 1230, 1125, 1060, 1015 cm$^{-1}$; MS (EI) 337 (MH+), 336 (M+.), 318, 155, 142 (100), 127, 69.

Analysis Calc'd. for $C_{20}H_{32}O_4$: C, 71.39; H, 9.59. Found: C, 70.92; H, 5.96.

EXAMPLE 27

4-Hydroxy-3-(1-oxo-9-octadecynyl)-2(5H)-furanone

To a stirring solution of 1.62 g (17.86 mmol) of tetronic acid in 50 mL of dimethylformamide is added 2.5 mL (17.86 mmol) of triethylamine and 652 mg of 4-dimethylaminopyridine at 0° C. Next, 3.71 g (19.35 mmol) of 1-(3-dimethylaminopropyl)-3-ethylcarbodiimide hydrochloride and 5.0 g (17.86 mmol) of stearolic acid are added and the reaction is stirred overnight at room temperature. The reaction is acidified with 1.0N HCl and extracted with three 50 mL portions of ether. The combined organic layers are dried over $MgSO_4$ and concentrated in vacuo affording crude compound. Pure material was obtained by flash chromatography with 10% methanol/ethyl acetate as eluant affording 3.3 g (56%) of 4-hydroxy-3-(1-oxo-9-octadecynyl)-2(5H)-furanone.

Spectral data follows: $^1H$ NMR ($CDCl_3$, 400 MHz) δ 4.616 (s, 2H, $CH_2OC=O$), 2.930 (t, 2H, O=$CCH_2$), 2.137 (m, 4H, C=$CCH_2$), 1.710 (m, 2H, O=$CCH_2CH_2$), 1.380 (m, 20H, $CH_2$), 0.881 (t, 3H, $CH_2CH_3$); IR (KBr) 3100, 2960, 2935, 2850, 1755, 1695, 1665, 1600, 1570, 1465, 1430, 1390, 1290, 1175, 1035, 1020, 865 cm$^{-1}$; MS (EI) 362 (M+.), 344, 260 (100), 246, 155, 142, 127, 95, 81, 67.

Analysis Calc'd. for $C_{22}H_{34}O_4$: C, 72.89; H, 9.45. Found: C, 73.23; H, 9.63.

EXAMPLE 28

4-Hydroxy-3-(1-oxooctadecyl)-2(5H)-furanone

To a stirring solution of 1.6 g (16 mmol) of tetronic acid in 75 mL of methylene chloride is added 2.5 mL (17.86 mmol) of triethylamine and 640 mg of 4-dimethylaminopyridine at 0° C. Next, 5.0 g (17.6 mmol) of stearoyl chloride is added and the reaction is stirred overnight at room temperature. The reaction is acidified with 1.0N HCl and extracted with two 100 mL portions of methylene chloride. The combined organic layers are dried over $MgSO_4$ and concentrated in vacuo affording crude compound. Pure material was obtained by trituration with ethyl acetate as affording 3.3 g (58%) of 4-hydroxy-3-(1-oxooctadecyl)-2(5H)-furanone.

Spectral data follows: $^1$H NMR (CDCl$_3$, 400 MHz) δ 4.615 (s, 2H, CH$_2$OC=O), 2.912 (t, 2H, O=CCH$_2$), 1.684 (m, 2H, O=CCH$_2$CH$_2$), 1.388-1.111 (m, 28H, CH$_2$), 0.881 (t, 3H, CH$_2$CH$_3$); IR (KBr) 3450, 2960, 2920, 2850, 1760, 1650, 1610, 1030, 885 cm$^{-1}$; MS (EI) 366 (M+.), 348, 155, 142(100), 127.

Analysis Calc'd. for C$_{22}$H$_{38}$O$_4$: C, 72.09; H, 10.45. Found: C, 72.42; H, 10.60.

EXAMPLE 29

3-[9-(4-Chlorophenoxy)-1-oxononyl]-4-hydroxy-2(5H)-furanone

To a stirring solution of 736 mg (7.36 mmol) of tetronic acid in 30 mL of dimethylformamide is added 1.2 mL (8.09 mmol) of triethylamine and 300 mg of 4-dimethylaminopyridine at 0° C. Next, 1.7 g (8.86 mmol) of 1-(3-dimethylaminopropyl)-3-ethylcarbodiimide hydrochloride and 2.6 g (8.06 mmol) of 9-(4-chlorophenoxy)-nonanoic acid are added and the reaction is stirred overnight at room temperature. The reaction is acidified with 1.0 N HCl and extracted with four 50 mL portions of ether. The combined organic layers are dried over MgSO$_4$ and concentrated in vacuo affording crude compound. Pure material is obtained by flash chromatography with 10% methanol/ethyl acetate as eluant affording 800 mg (30%) of 3-[9-(4-chlorophenoxy)-1-oxononyl]-4-hydroxy-2(5H)-furanone.

Spectral data follows: $^1$H NMR (CDCl$_3$, 400 MHz) δ 7.216 (d, 2H, Ar), 6.813 (d, 2H, Ar), 4.614 (s, 2H, CH$_2$OC=O), 3.911 (t, 2H, OCH$_2$Ar), 2.912 (t, 2H, O=CCH$_2$), 1.742 (m, 4H, CH$_2$), 1.370 (m, 8H, CH$_2$); IR (KBr) 3220, 2940, 2860, 1770, 1745, 1660, 1610, 1600, 1495, 1475, 1435, 1395, 1345, 1290, 1270, 1250, 1210, 1175, 1130, 1110, 1100, 1060, 1010, 825 cm$^{-1}$; MS (CI+) 367 (MH+), 277, 275 (100), 257, 239, 91, 61.

Analysis Calc'd for C$_{19}$H$_{23}$ClO$_5$: C, 62.21; H, 6.32. Found: C, 61.82; H, 6.25.

EXAMPLE 30

Hexylcarbamic acid 5-(2,5-dihydro-4-hydroxy-2-oxo-3-furanyl)-5-oxo-1,2-pentanediyl ester To a stirring solution of 234 mg (2.34 mmol) of tetronic acid in 20 mL of dimethylformamide is added 400 μL (2.57 mmol) of triethylamine and 200 mg of 4-dimethylaminopyridine at 0° C. Next, 600 mg (3.12 mmol) of 1-(3-dimethylaminopropyl)-3-ethylcarbodiimide and 1.0 g (2.57 mmol) of 4,5-bis[[(hexylamino)carbonyl]oxy]pentanoic acid are added and the reaction is stirred 3 days at room temperature. The reaction is acidified with 1.0N HCl and extracted with three 100 mL portions of ether. The combined organic layers are dried over MgSO$_4$ and concentrated in vacuo affording 636 mg (58%) of hexylcarbamic acid 5-(2,5-dihydro-4-hydroxy-2-oxo-3-furanyl)-5-oxo-1,2-pentanediyl ester.

Spectral data follows: $^1$H NMR (CDCl$_3$, 400 MHz) δ 4.896 (m, 1H, HCOC=O), 4.792 (m, 2H, NH), 4.628 (s, 2H, CH$_2$OC=O), 4.157 (m, 2H, H$_2$COC=O), 3.152 (m, 6H, NHCH$_2$, O=CCH$_2$), 2.047 (m, 2H, O=CCH$_2$CH$_2$), 1.485 (m, 4H, HNCH$_2$CH$_2$), 1.289 (m, 12H, CH$_2$), 0.885 (t, 6H, CH$_2$CH$_3$); IR (KBr) 3350, 2960, 2935, 2860, 1750, 1700, 1645, 1580, 1550, 1465, 1275, 1040 cm$^{-1}$; MS (pos.ion FAB) 515 (MNa++), 493 (MNa+), 370, 350, 181, 102, 55, 43 (100).

Analysis Calc'd. for C$_{23}$H$_{38}$N$_2$O$_8$: C, 58.71; H, 8.14; N, 5.95. Found: C, 58.77; H, 8.19; N, 5.77.

EXAMPLE 31

Dodecylcarbamic acid 5-(2,5-dihydro-4-hydroxy-2-oxo-3-furanyl)-5-oxo-1,2-pentanediyl ester A) 4,5-Bis[[(Dodecylamino)carbonyl]oxy]pentanoic acid To a stirring solution 1.9 g (9.47 mmol) of 1.9 g (9.47 mmol) of the (Z)-5-[[(1,1-dimethylethyl)dimethylsilyl]oxy]-1-pentene-1,2-diol in 20 mL of methylene chloride is added 3.2 mL (23 mmol) of triethylamine and 4.8 g (9.47 mmol) of dodecyl isocyanate at 0° C. and the reaction is stirred for 2 days at room temperature. The reaction is diluted with methylene chloride and washed with 1.0N HCl, saturated sodium bicarbonate, and brine, dried over sodium sulfate and concentrated in vacuo. The resulting dicarbamate is dissolved in 20 mL of tetrahydrofuran and treated with 20 mL of 1.0M tetrabutylammonium fluoride in tetrahydrofuran and the reaction is stirred overnight at room temperature. The reaction mixture was poured into water and extracted with three 100 mL portions of ether. The combined organic layers are dried over MgSO$_4$ and concentrated in vacuo affording crude compound. Pure material is obtained by flash chromatography with ethyl acetate as eluant affording 4.1 g (80%) of alcohol. Next, 12 mL of 2.0M Jones reagent is added at 0° C. to a stirring solution of 4.1 g (7.62 mmol) of the alcohol in 75 mL of acetone and the reaction is stirred for 4 hours. The reaction is poured into water and extracted with three 100 mL portions of ether. The combined organic layers are dried over MgSO$_4$ and concentrated in vacuo, affording 2.1 g (50%) of 4,5-bis[[dodecylamino)carbonyl]oxy]pentanoic acid.

Spectral data follows: $^1$H NMR (CDCl$_3$, 400 MHz) δ 4.961 (m, 1H, HCOC=O), 4.741 (m, 2H, NH), 4.110 (m, 2H, H$_2$COC=O), 3.130 (m, 4H, HNCH$_2$), 2.425 (m, 2H, HO$_2$CCH$_2$), 1.897 (m, 2H, HO$_2$CCH$_2$CH$_2$), 1.466 (m, 4H, HNCH$_2$CH$_2$), 1.242 (s, 3H, CH$_2$), 0.866 (t, 6H, CH$_2$CH$_3$); IR (KBr) 3450, 2930, 2860, 1700, 1660, 1470, 1280 cm$^{-1}$; MS (pos.ion FAB) 579 (M+Na), 557 (MH+), 328 (100), 230, 186, 117, 91, 73, 57, 43, 30.

Analysis Calc'd. for C$_{31}$H$_{60}$N$_2$O$_6$: C, 66.87; H, 10.86; N, 5.03, Found: C, 67.30; H, 11.06; N, 5.06.

B) Dodecylcarbamic acid 5-(2,5-dihydro-4-hydroxy-2-oxo-3-furanyl)-5-oxo-1,2-pentanediyl ester To a stirring solution of 163 mg (1.63 mmol) of tetronic acid in 20 mL of dimethylformamide is added 250 μL (1.8 mmol) of triethylamine and 100 mg of 4-dimethylaminopyridine at 0° C. Next, 400 mg (2.08 mmol) of 1-(3-dimethylaminopropyl)-3-ethylcarbodiimide hydrochloride and 1.0 g (1.8 mmol) of 4,5-bis[[(dodecylamino)carbonyl]oxy]pentanoic acid are added and the reaction is stirred 3 days at room temperature. The reaction is acidified with 1.0N HCl and extracted with three 100 mL portions of ether. The combined organic layers are dried over MgSO$_4$ and concentrated in vacuo affording crude compound. Pure material is obtained by flash chromatography with 10% methanol/ethyl acetate as eluant affording 500 mg (50%) of dodecylcarbamic acid 5-(2,5-dihydro-4-hydroxy-2-oxo-3-furanyl)-5-oxo-1,2-pentanediyl ester.

Spectral data follows: $^1$H NMR (CDCl$_3$, 400 MHz) δ 4.896 (m, 1H, HCOC=O), 4.792 (m, 2H, NH), 4.628 (s, 2H, CH$_2$OC=O), 4.157 (m, 2H, H$_2$COC=O), 3.152 (m, 6H, O=CCH$_2$, NHCH$_2$), 2.047 (m, 2H, O=CCH$_2$CH$_2$), 1.485 (m, 4H, NHCH$_2$CH$_2$), 1.289 (m, 36H, CH$_2$), 0.885 (t, 6H, CH$_2$CH$_3$); IR (KBr) 3350, 2960, 2935, 2860, 1750, 1700, 1645, 1580, 1550, 1465, 1275, 1040 cm$^{-1}$; MS (pos.ion FAB) 683 (MNa++), 661 (MNa+), 237, 221,186,131,91,73,57 (100).

Analysis Calc'd. for C$_{35}$H$_{62}$N$_2$O$_8$: C, 65.80; H, 9.78; N, 4.38, Found: C, 66.19; H, 9.86; N, 4.26.

EXAMPLE 32

4-Hydroxy-3-[6-[4-[(4-chlorophenyl)methoxyphenoxy]]1-oxohexyl]-2(5H)-furanone

To a stirring solution of 757 mg (7.57 mmol) of tetronic acid in 50 mL of dimethylformamide is added 1.20 mL (8.83 mmol) of triethylamine and 400 mg of 4-dimethylaminopyridine at 0° C. Next, 2.00 g (8.3 mmol) of 1-(3-dimethylaminopropyl)-3-ethylcarbodiimide hydrochloride and 2.88 g (8.3 mmol) of 6-[4-(4-chlorophenyl)methoxyphenoxy]hexanoic acid are added and the reaction mixture is stirred 3 days at room temperature. The reaction is acidified with 1.0N HCl and extracted three times with ethyl acetate. The combined organic layers are dried over MgSO$_4$ and concentrated in vacuo giving a yellow oil. Pure material was obtained by flash chromatography on a 40 mm×150 mm silica column eluting with 10% methanol/ethyl acetate giving 800 mg (25%) of 4-hydroxy-3-[6-[4-[(4-chlorophenyl)methoxyphenoxy]]-1-oxohexyl]-2(5H)-furanone.

Spectral data follows: $^1$H NMR (CDCl$_3$, 400 MHz) δ 7.338 (s, 4H, Ar), 6.849 (d, 2H, Ar), 6.811 (d, 2H, Ar), 4.966 (s, 2H, CH$_2$Ar), 4.611 (s, 2H, CH$_2$OC=O), 3.899 (t, 2H, CH$_2$OAr), 2.964 (t, 2H, O=CCH$_2$), 1.824-1.546 (m, 6H, CH$_2$); IR (KBr) 3420, 2945, 2860, 1770, 1660, 1615, 1515, 1245, 1030 cm$^{-1}$; MS (EI) 430 (M+), 197, 127, 125 (100).

Analysis Calc'd. for C$_{23}$H$_{23}$O$_6$Cl: C, 64.11; H, 5.38. Found: C, 63.98; H, 5.45.

EXAMPLE 33

4-Hydroxy-3-[6-[4-(hexyloxy)phenoxy]-1-oxohexyl]-2(5H)-furanone

To a stirring solution of 876 mg (8.76 mmol) of tetronic acid in 50 mL of dimethylformamide is added 1.40 mL (10.30 mmol) of triethylamine and 400 mg of 4-dimethylaminopyridine at 0° C. Next, 2.00 g (8.3 mmol) of 1-(3-dimethylaminopropyl)-3-ethylcarbodiimide hydrochloride and 2.97 g (8.3 mmol) of 6-[4-(hexyloxy)phenoxy]hexanoic acid are added and the reaction mixture is stirred 3 days at room temperature. The reaction is acidified with 1.0N HCl and extracted three times with ethyl acetate. The combined organic layers are dried over MgSO$_4$ and concentrated in vacuo giving a yellow oil. Pure material was obtained by flash chromatography on a 40 mm×150 mm silica column eluting with 10% methanol/ethyl acetate giving 1.1 g (32%) of 4-hydroxy-3-[6-[4-(hexyloxy)phenoxy]-1-oxohexyl]-2(5H)-furanone.

Spectral data follows: $^1$H NMR (CDCl$_3$, 400 MHz) δ 4.601 (s, 2H, CH$_2$OC=O), 3.910 (s, 4H, CH$_2$OAr), 2.951 (t, 2H, O=CCH$_2$), 1.815-1.309 (m, 14H, CH$_2$), 0.918 (t, 3H, CH$_2$CH$_3$); IR (KBr) 2950, 2880, 1770, 1680, 1650, 1615, 1520, 1250, 1040 cm$^{-1}$; MS (CI) 391 (MH+), 349, 291, 117 (100).

Analysis Calc'd for C$_{22}$H$_{30}$O$_6$: C, 67.67; H, 7.74. Found: C, 67.70; H, 7.70.

EXAMPLE 34

4-Hydroxy-3-[7-(4-chlorophenoxy)-1-oxoheptyl]-2(5H)-furanone

To a stirring solution of 1.00 g (10 mmol) of tetronic acid in 40 mL of dimethylformamide is added 1.51 mL (11.11 mmol) of triethylamine and 402 mg (3.33 mmol) of 4-dimethylaminopyridine at 0° C. Next, 2.29 g (11.97 mmol) of 1-(3-dimethylaminopropyl)-3-ethylcarbodiimide hydrochloride and 3.07 g (11.97 mmol) of 7-(4-chlorophenoxy)heptanoic acid are added and the reaction mixture is stirred 2 days at room temperature. The reaction is acidified with 1.0N HCl and extracted three times with ethyl acetate. The combined organic layers are dried over Na$_2$SO$_4$ and concentrated in vacuo giving a yellow oil. Pure material was obtained by flash chromatography on a 40 mm×150 mm silica column eluting with 10% methanol/ethyl acetate giving 1.50 g (44%) of 4-hydroxy-3-[7-(4-chlorophenoxy)-1-oxoheptyl]-2(5H)furanone.

Spectral data follows: $^1$H NMR (CDCl$_3$,400 MHz) δ 7.290 (d, 2H, Ar), 6.928 (d, 2H, Ar), 4.488 (s, 2H, CH$_2$OC=O), 3.924 (t, 2H, CH$_2$OAr), 2.711 (t, 2H, O=CCH$_2$), 1.694-1.298 (m, 8H,CH$_2$); IR (KBr) 3210, 2960, 2880, 1773, 1760, 1665, 1620, 1500, 1480, 1440, 1355, 1060 cm$^{-1}$; MS (EI) 338 (M+), 211 (100), 193, 128.

Analysis Calc'd. for C$_{17}$H$_{19}$O$_5$Cl.0.25 H$_2$O: C, 59.48; H, 5.69, Found: C, 59.27; H, 5.79.

EXAMPLE 35

3-[(Z)-10-(4-chlorophenyl)-1-oxo-9-decenyl]-4-hydroxy-2(5H)-furanone

A) (Z)-10-(4-chlorophenyl)-9-decenoic acid

To a stirring solution of 20.0 g (79.7 mmol) of methyl-9-bromononate in 50 mL of acetonitrile is added 21.0 g (79.7 mmol) of triphenylphosphine and allowed to reflux overnight. The reaction mixture is concentrated in vacuo affording 41.0 g (100%) of phosphonium salt. Next, 8.5 g (16.5 mmol) of the phosphonium salt is dissolved in 100 mL of tetrahydrofuran and the reaction is cooled to −78° C. 17.0 mL (17.0 mmol) of 1.0M LiHMDS is added dropwise and the reaction mixture is stirred for 1 hour. Then, 2.3 g (16.5 mmol) of 4-chlorobenzaldehyde is added and the reaction mixture is stirred overnight with gradual warming to room temperature. The reaction mixture is poured into water and extracted with three 30 mL portions of ether. The combined organic layers are dried over MgSO$_4$ and concentrated in vacuo affording crude product. Pure material was obtained by flash chromatography with 10% ethyl acetate/hexane as eluant affording 600 mg (12%) of olefin. Next, 2.0 g of KOH is added at room temperature to a solution of 600 mg (1.93 mmol) of olefin in a 3:1 solution of methanol/water and the reaction mixture is stirred for 2 hours. The reaction mixture is acidified with 1.0N HCl and extracted with three 50 mL portions of ether. The organic layers are dried over MgSO$_4$ and concentrated in vacuo affording 500 mg (87%) of (Z)-10-(4-chlorophenyl)-9-decenoic acid.

Spectral data follows: $^1$H NMR (CDCl$_3$, 400 MHz) δ 7.287 (d, 2H, Ar), 7.186 (d, 2H, Ar), 6.343 (d, 1H, HC=CH), 5.665 (m, 1H, HC=CH), 2.301 (m, 4H, HOCCH$_2$, C=CCH$_2$), 1.618 (m, 2H, HO$_2$CCH$_2$CH$_2$), 1.433 (m, 2H, C=CCH$_2$CH$_2$), 1.304 (m, 6H, CH$_2$).

B) 3-[(Z)-10-(4-chlorophenyl)-1-oxo-9-decenyl]-4-hydroxy-2(5H)-furanone

To a stirring solution of 117.0 mg (117.0 mmol) of tetronic acid in 10 mL of dimethylformamide is added 181 μL (1.3 mmol) of triethylamine and 50 mg of 4-dimethylaminopyridine at 0° C. Next, 264 mg (1.37 mmol) of 1-(3-dimethylaminopropyl)-3-ethylcarbodiimide hydrochloride and 380 mg of (Z)-10-(4-chlorophenyl)-9-decenoic acid are added and the reaction mixture is stirred 2 days at room temperature. The reaction mixture is acidified with 1.0N HCl and extracted with three 50 mL portions of ether. The combined organic layers are dried over MgSO$_4$ and concentrated in vacuo affording crude product. Pure material was obtained by flash chromatography with 10% methanol/ethyl acetate as eluant affording 100 mg (25%) of 3-[(Z)-10-(4-chlorophenyl)-1-oxo-9-decynyl]-4-hydroxy-2(5H)-furanone.

Spectral data follows: $^1$H NMR (CDCl$_3$, 400 MHz) δ 7.221 (d, 2H, Ar), 7.115 (d, 2H, Ar), 6.279 (d, 1H, HC=CH), 5.596 (d of t, 1H, HC=CH), 4.544 (s, 2H, CH$_2$OC=O), 2.828 (t, 2H, O=CCH$_2$), 2.202 (m, 2H, C=CCH$_2$), 1.617 (m, 2H, O=CCH$_2$CH$_2$), 1.266 (m, 8H, CH$_2$); IR (KBr) 3450, 3200, 2950, 2880, 1785, 1735, 1675, 1620, 1500, 1475, 1450, 1400, 1360, 1270, 1240, 1110, 1070, 1025, 885 cm$^{-1}$; MS (EI) 364 (MH+), 362 (MH+), 328, 327, 309, 279, 167, 151, 149 (100), 138, 127, 95, 71.

Analysis Calc'd. for C$_{20}$H$_{23}$ClO$_4$ : C, 66.20; H, 6.39. Found : C, 66.58; H, 6.43.

EXAMPLE 36

4-Hydroxy-3-((E)-1-oxo-9-octadecenyl)-2(5H)-furanone

To a stirring solution of 1.0 g (10.0 mmol) of tetronic acid in 32 mL of dimethylformamide is added 1.53 mL (10.98 mmol) of triethylamine and 400 mg of 4-dimethylaminopyridine at 0° C. Next, 2.28 g (11.98 mmol) of 1-(3-dimethylaminopropyl)-3-ethylcarbodiimide hydrochloride and 3.1 g (10.98 mmol) of elaidic acid are added and the reaction mixture is stirred for 2 days at room temperature. The reaction mixture is acidified with 1.0N HCl and extracted with four 100 mL portions of ether. The combined organic layers are dried over MgSO$_4$ and concentrated in vacuo. Trituration of the crude product in ether affords 1.2 g (33%) of 4-hydroxy-3-((E)-1-oxo-9-octadecenyl)-2(5H)-furanone.

Spectral data follows: $^1$H NMR (CDCl$_3$, 400 MHz) δ 5.367 (m, 2H, HC=CH), 4.602 (s, 2H, CH$_2$OC=O), 2.897 (t, 2H, O=CCH$_2$), 1.943 (m, 4H, C=CCH$_2$), 1.689 (m, 2H, O=CCH$_2$CH$_2$), 1.314 (m, 20H, CH$_2$), 0.867 (t, 3H, CH$_2$CH$_3$); IR (KBr) 3420, 2920, 2840, 1770, 1750, 1660, 1615, 1455, 1430, 1385, 1340, 1265, 1235, 1220, 1200, 1120, 1050, 1010, 960, 940, 830 cm$^{-1}$; MS (EI) 364 (M+·), 346, 155, 142 (100), 127.

Analysis Calc'd. for C$_{22}$H$_{36}$O$_4$: C, 72.49; H, 9.95. Found: C, 72.50; H, 9.89.

EXAMPLE 37

3-[6-(4-Heptylphenoxy)-1-oxohexyl]-4-hydroxy-2(5H)-furanone

To a stirring solution of 1.1 g (10.98 mmol) of tetronic acid in 25 mL of dimethylformamide is added 1.53 mL (10.98 mmol) of triethylamine and 400 mg of 4-dimethylaminopyridine at 0° C. Next, 2.28 g (11.98 mmol) of 1-(3-dimethylaminopropyl)-3-ethylcarbodiimide hydrochloride and 3.38 g (10.98 mmol) of 6-(4-heptylphenoxy)heptanoic acid are added and the reaction mixture is stirred for 3 days at room temperature. The reaction mixture is acidified with 1.0N HCl and extracted with three 200 mL portions of ether. The combined organic layers are dried over MgSO$_4$ and concentrated in vacuo. Trituration of the crude product in ethyl acetate/hexane affords 2.1 g (50%) of 3-[6-(4-heptylphenoxy)-1-oxohexyl]-4-hydroxy-2(5H)-furanone.

Spectral data follows: $^1$H NMR (CDCl$_3$, 400 MHz) δ 7.071 (d, 2H, Ar), 6.797 (d, 2H, Ar), 4.608 (s, 2H,CH$_2$OC=O), 3.935 (t, 2H, OCH$_2$), 2.949 (t, 2H, O=CCH$_2$), 2.523 (t, 2H, CH$_2$Ar), 1.786 (m, 4H, O=CCH$_2$CH$_2$), 1.573 (m, 4H, ArCH$_2$CH$_2$), 1.284 (m, 8H, CH$_2$), 0.873 (t, 3H, CH$_2$CH$_3$); IR (KBr) 3450, 3200, 2920, 2850, 1780, 1750, 1660, 1615, 1510, 1460, 1430, 1385, 1340, 1245, 1175, 1125, 1050, 1010, 830 cm$^{-1}$; MS (EI) 388 (M+·), 197, 192, 127, 107 (100).

Analysis Calc'd. for C$_{23}$H$_{32}$O$_5$: C, 71.10; H, 8.30. Found: C, 71.23; H, 8.36.

EXAMPLE 38

(Z)-9-Octadecanoic acid 4-(2,5-dihydro-4-hydroxy-2-oxo-3-furanyl)-4-oxobutanoic ester A) (Z)-9-octadecenoic acid 4-hydroxybutyl ester To a stirring solution of 2.0 g (7.0 mmol) of oleic acid and 1.6 g (7.0 mmol) of 2-(4-bromobutoxy)tetrahydro-2H-pyran in 20 mL of tetrahydrofuran is added 2.3 g (7.1 mmol) of cesium carbonate and the reaction mixture is stirred overnight at room temperature. The reaction mixture is poured into water and extracted with three 100 mL portions of ether. The combined organic layers are dried over MgSO$_4$ and concentrated in vacuo affording 2.9 g (100%) of (Z)-9-octadecenoic acid 4-[(tetrahydro-2H-pyran-2-yl)oxy]butyl ester. Next, 500 mg of Dowex 50W 8X resin is added to a stirring solution of 2.9 g (7.0 mmol) of (Z)-9-octadecenoic acid 4-[(tetrahydro-2H-pyran-2-yl)oxy]butyl ester in 100 mL of 1:1 tetrahydrofuran/methanol and the reaction mixture is stirred overnight at room temperature. The reaction mixture is filtered and concentrated in vacuo affording 2.4 g (100%) of alcohol. Next, 11 mL of 2.0M Jones reagent is added at 0° C. to a stirring solution of 2.4 g (7.0 mmol) of alcohol in 75 mL of acetone and the reaction mixture is stirred for 2 hours. The reaction mixture is poured into water and extracted with three 50 mL portions of ether. The combined organic layers are dried over MgSO$_4$ and concentrated in vacuo affording 2.1 g (81%) of title compound.

Spectral data follows: $^1$H NMR (CDCl$_3$, 400 MHz) δ 5.332 (m, 2H, HC=CH), 4.126 (t, 2H, O=COCH$_2$), 2.405 (t, 2H, HO$_2$CCH$_2$), 2.283 (t, 2H, O(C=O)CH$_2$), 2.003 (m, 4H, C=CCH$_2$), 1.595 (m, 2H, O=CCH$_2$CH$_2$), 1.270 (m, 22H, CH$_2$), 0.867 (t, 3H, CH$_2$CH$_3$).

B) (Z)-9-Octadecanoic acid 4-(2,5-dihydro-4-hydroxy-2-oxo-3-furanyl)-4-oxobutanoic ester To a stirring solution of 570 mg (5.7 mmol) of tetronic acid in 50 mL of dimethylformamide is added 795 μL (5.7 mmol) of triethylamine and 400 mg of 4-dimethylaminopyridine at 0° C. Next, 1.2 g (6.26 mmol) of 1-(3-dimethylaminopropyl)-3-ethylcarbodiimide hydrochloride and 2.1 g of (Z)-9-octadecenoic acid 4-hydroxybutyl ester are added and the reaction mixture is stirred overnight at room temperature. The reaction mixture is acidified with 1.0N HCl and extracted with three 100 mL portions of ethyl acetate. The combined organic layers are dried over MgSO$_4$ and concentrated in vacuo affording crude product. Pure material is obtained by flash chromatography with 10% methanol-/ethyl acetate as eluant affording 1.8 g (72%) of (Z)-9-octadecenoic acid 4-(2,5-dihydro-4-hydroxy-2-oxo-3-furanyl)-4-oxobutanoic ester.

Spectral data follows: $^1$H NMR (CDCl$_3$, 400 MHz) δ 5.332 (m, 2H, HC=CH), 4.616 (s, 2H, CH$_2$OC=O), 4.126 (t, 2H, O=COCH$_2$), 3.004 (t, 2H, O=CCH$_2$), 2.283 (t, 2H, O(C=O)CH$_2$), 2.003 (m, 4H, C=CCH$_2$), 1.595 (m, 2H, O=CCH$_2$CH$_2$), 1.270 (m, 22H, CH$_2$), 0.867 (t, 3H, CH$_2$CH$_3$); IR (KBr) 3025 2935, 2865, 1775, 1735, 1705, 1610, 1520, 1470, 1440, 1230, 1180, 1045, 1015 cm$^{-1}$; MS (CI+) 451 (MH+), 297, 283, 265, 183, 169 (100), 102.

Analysis Calc'd. for C$_{26}$H$_{42}$O$_6$: C, 69.30; H, 9.39. Found: C, 69.08; H, 9.37.

EXAMPLE 39

4-Hydroxy-3-[6-(1,1,3,3-tetramethylbutyl)phenoxy)-1-oxohexyl]2(5H)-furanone

To a stirring solution of 329 mg (3.29 mmol) of tetronic acid in 15 mL of dimethylformamide is added 458 μL (3.29 mmol) of triethylamine and 220 mg (1.765 mmol) of 4-dimethylaminopyridine at 0° C. Next, 681 mg (3.58 mmol) of 1-(3-dimethylaminopropyl)-3-ethylcarbodiimide hydrocholoride and 1.0 g (3.29 mmol) of 6-(1,1,3,3-tetramethybutyl)phenoxy)hexanoic acid are added and the reaction mixture is stirred overnight at room temperature. The reaction is acidified with 1.0N HCl and extracted three times with ether. The combined organic layers are dried over MgSO$_4$ and concentrated in vacuo giving a yellow solid. Flash chromatography on a 40 mm×150 mm silica gel column eluting with 10% methanol/ethyl acetate gives 650 mg (50%) of 4-hydroxy-3-[6-(1,1,3,3-tetramethylbutyl)phenoxy)-1-oxohexyl]-2(5H)-furanone.

Spectral data follows: $^1$H NMR (CDCl$_3$, 400 MHz) δ 7.255 (d, 2H, Ar), 6.778 (d, 2H, Ar), 4.599 (s, 2H, CH$_2$OC=O), 3.935 (t, CH$_2$OAr), 2.947 (t, 2H, O=CCH$_2$), 1.824–1.573 (m, 6H, CH$_2$), 1.688 (s, 2H, CH$_2$), 1.330 (3, 6H, C(CH$_3$)$_2$), 0.705 (s, 9H, t-Bu); IR (KBr) 2960, 2870, 1775, 1695, 1655, 1610, 1510, 1250, 1040 cm$^1$; MS (EI) 402 (M+), 331 (100), 127.

Analysis Calc'd. for C$_{24}$H$_{34}$O$_5$: C, 71.61; H, 8.51. Found: C, 71.70; H, 8.42.

EXAMPLE 40

((Z)-9-octadecynyl)carbamic acid 1-[[((E)-3,7-Dimethyl-2,6-octadecadienyl)oxy]methyl]-4-(2,5-dihydro-4-hydroxy-2-oxo-3-furanyl)-4-oxobutyl ester A) 5-[((E)-3,7-Dimethyl-2,6-octadienyl)oxy]-4-[[((Z)-9-octadecenylamino)carbonyl]oxy]pentanoic acid To a stirring suspension of 140 mg (4.6 mmol) of 80% NaH in 5 mL of tetrahydrofuran is added 1.07 g (4.6 mmol) of (Z)-5-[[(1,1-dimethylethyl)dimethylsilyl]oxy]-1-pentene-1,2-diol at 0° C. and the reaction mixture is stirred for 1 hour. Next, 1.0 g (4.6 mmol) of geranyl bromide is added and the reaction is stirred overnight at room temperature. The reaction mixture is poured into water and extracted with three 50 mL portions of ethyl acetate. The combined organic layers are dried over MgSO$_4$ and concentrated in vacuo affording 1.7 g (100%) of (E)-5-[[(1,1-dimethylethyl)dimethylsilyl]oxy]-1-[(3,7-dimethyl-2,6-octadienyl)oxy]-2-pentanol. Next, 1.6 g (4.3 mmol) of (E)-5-[[(1,1-dimethylethyl)dimethylsilyl]oxy]-1-[(3,7-dimethyl-2,6-octadienyl)oxy]-2-pentanol and 800 μL (5.73 mmol) of triethylamine in 20 mL of methylene chloride are added at 0° C. to a stirring solution of 13.3 mL of 20% phosgene in toluene and the reaction mixture is stirred for 1 hour. The reaction mixture is concentrated in vacuo and redissolved in 20 mL of tetrahydrofuran. Next, 1.3 g (4.6 mmol) of oleyl amine is added and the reaction mixture is stirred for 2 hours. The reaction mixture is poured into water and extracted with three 50 mL portions of ether. The organic layers are dried over MgSO$_4$ and concentrated in vacuo affording crude product. Pure material is obtained by flash chromatography with 10% ethyl acetate/hexane as eluant affording 1.67 g (67%) of (Z)-9-octadecenylcarbamic acid (E)-5-[[(1,1-dimethylethyl)-dimethylsilyl]oxy]-1-[[(3,7-dimethyl-2,6-octadienyl)oxy]methyl]butyl ester. Next, 5 mL of 1.0M tetrabutylammonium fluoride in tetrahydrofuran is added to a stirring solution of 1.67 g (2.5 mmol) of (Z)-9-octadecenylcarbamic acid (E)-5-[[(1,1-dimethylethyl)dimethylsilyl]oxy]-1-[[(3,7-dimethyl-2,6-octadienyl)oxy]methyl]butyl ester in 5 mL of tetrahydrofuran and the reaction mixture is stirred overnight. The reaction mixture is poured into water and extracted with three 50 mL portions of ether. The combined organic layers are dried over MgSO$_4$ and concentrated in vacuo affording crude product. Pure material is obtained by flash chromatography with 10% ethyl acetate/hexane as eluant affording 722 mg (54%) of (Z)-9-octadecenylcarbamic acid (E)-1-[[(3,7-dimethyl-2,6-octadienyl)oxy]methyl]-4-hydroxybutyl ester. Next, 2 mL of 2.0M Jones reagent is added at 0° C. to a solution of 722 mg (1.33 mmol) of (Z)-9-octadecenylcarbamic acid (E)-1-[[(3,7-dimethyl-2,6-octadienyl)oxy]methyl]-4-hydroxybutyl ester in 12 mL of acetone and the reaction is stirred for 3 hours. The reaction is poured into water and extracted with three 50 mL portions of ether. The combined organic layers are dried over MgSO$_4$ and concentrated in vacuo affording crude product. Pure material was obtained by flash chromatography with 35% ethyl acetate/hexane as eluant affording 226 mg (30%) of 5-[((E)-3,7-dimethyl-2,6-octadienyl)oxy]-4-[[((Z)-9-octadecenylamino)carbonyl]oxy]pentanoic acid.

Spectral data follows: $^1$H NMR (CDCl$_3$, 400 MHz) δ 5.336 (m, 3H, HC=CH), 5.076 (m, 1H, HC=C), 4.903 (m, 1H, HCOC=O), 4.751 (m, 1H, NH), 4.001 (m, 2H, OCH$_2$), 3.487 (d, 2H, OCH$_2$), 3.143 (d, 2H, O=CCH$_2$, HNCH$_2$), 2.422 (t, 2H, HO$_2$CCH$_2$), 2.076 (m, 8H, C=CCH$_2$), 1.666 (s, 3H, C=CCH$_3$), 1.640 (s, 3H, C=CCH$_3$), 1.588 (s, 3H, C=CCH$_3$), 1.466 (m, 4H, O=CCH$_2$CH$_2$, NHCH$_2$CH$_2$), 1.256 (m, 22H, CH$_2$), 0.869 (t, 3H, CH$_2$CH$_3$); IR (KBr) 3350, 2940, 2870, 1725, 1545, 1455, 1380, 1250, 1130 cm$^{-1}$; MS (CI+) 564 (MH+), 429, 428, 410, 153, 137 (100), 135, 117, 99, 81.

Analysis Calc'd. for C$_{34}$H$_{61}$NO$_5$: C, 72.42; H, 10.90; N, 2.48. Found: C, 72.13; H, 10.53; N, 2.41.

B) ((Z)-9-octadecynyl)carbamic acid 1-[[((E)-3,7-Dimethyl-2,6-octadecadienyl)oxy]methyl]-4-(2,5-dihydro-4-hydroxy-2-oxo-3-furanyl)-4-oxobutyl ester To a stirring solution of 146 mg (1.46 mmol) of tetronic acid in 10 mL of dimethylformamide is added 200 μL (1.46 mmol) of triethylamine and 75 mg of 4-dimethylaminopyridine at 0° C. Next, 300 mg (1.56 mmol) of 1-(3-dimethylaminopropyl)-3-ethylcarbodiimide hydrochloride and 810 mg (1.46 mmol) of 5-[((E)-3,7-dimethyl-2,6-octadienyl)oxy]-4-[[((Z)-9-octadecenylamino)-carbonyl]oxy]pentanoic acid are added and the reaction mixture is stirred for 2 days at room temperature. The reaction mixture is acidified with 1.0N HCl and extracted with three 50 mL portions of ether. The combined organic layers are dried over MgSO$_4$ and concentrated in vacuo affording crude product. Pure material was obtained by flash chromatography with 10% methanol/ethyl acetate as eluant affording 800 mg (86%) of ((Z)-9-octadecynyl)carbamic acid 1-[[((E)-3,7-dimethyl-2,6-octadecadienyl)oxy]methyl]-4-(2,5-dihydro-4-hydroxy-2-oxo-3-furanyl)-4-oxobutyl ester.

Spectral data follows: $^1$H NMR (CDCl$_3$, 400 MHz) δ 5.351 (m, 3H, HC=CH), 5.090 (m, 1H, HC=C), 4.918 (m, 1H, HCOC=O), 4.747 (m, 1H, NH), 4.667 (s, 2H, CH$_2$OC=O), 4.039 (m, 2H, OCH$_2$), 3.515 (d, 2H, OCH$_2$), 3.136 (m, 2H, NHCH$_2$), 3.033 (m, 2H, O=CCH$_2$), 2.076 (m 8H, C=CCH$_2$), 1.683 (s, 3H, C=CCH$_3$), 1.658 (s, 3H, C=CCH$_3$), 1.605 (s, 3H, C=CCH$_3$), 1.483 (m, 4H, O=CCH$_2$CH$_2$, HNCH$_2$CH$_2$), 1.256 (m, 22H, CH$_2$), 0.865 (t, 3H, CH$_2$CH$_3$); IR (film) 3360, 2930, 2860, 1775, 1725, 1705, 1605, 1525, 1460, 1440, 1375, 1245, 1125, 1040, 1015 cm$^{-1}$; MS (CI+) 646 (MH+), 511, 510, 492, 412, 411, 410 (100), 209, 199, 153, 137, 81.

Analysis Calc'd. for C$_{38}$H$_{63}$NO$_7$: C, 70.66; H, 9.83; N, 2.17. Found: C, 70.60; H, 9.48; N, 1.92.

EXAMPLE 41

4-Hydroxy-3-[10-(4-chlorophenyl)-1-oxodecyl]-2(5H)-furanone

To a solution of 165 mL (165 mmol) of a 1.0M solution of boranetetrahydrofuran complex in tetrahydrofuran in 200 mL of dry diethyl ether at 0° C. is added dropwise 25.0 g (123 mmol) of azelaic acid monomethyl ester, added at such a rate as to prevent excessive release of gas and exothermicity. The solution is allowed to warm to room temperature overnight and is worked up by slowly adding water until gas evolution ceases. Then solid potassium carbonate is added and the organic layer is separated. The aqueous layer is extracted three times with diethyl ether. The combined extracts are washed with brine, dried over Na$_2$SO$_4$, filtered, and concentrated in vacuo to give 8-carbomethoxyoctan-1-ol as a colorless oil.

This crude oil is dissolved in 800 mL of dry dichloromethane and 417 mg of 2,2,6,6-tetramethyl-1-piperidinyloxy, free radical is added followed by 4.25 g of sodium bromide in 42 mL of water. The solution is cooled to 0°-10° C. and 417 mL of a 5.25% solution of NaOCl (Clorox) and 8.34 g of sodium bicarbonate are added dropwise to the stirring solution. The solution is stirred an additional hour after addition was complete. The organic layer is separated, washed with aqueous sodium thiosulfate, followed by a saturated sodium bicarbonate solution and then by brine. The solution is dried over Na$_2$SO$_4$, filtered, and concentrated in vacuo to give a 19.0 g (83%) of 8-carbomethoxyoctan-1-al as a light yellow oil.

To a solution of 18.2 g (43 mmol) of 4-chlorobenzyltriphenylphosphonium chloride in 200 mL of dry tetrahydrofuran at −78° C. is added dropwise, 30.7 mL (43 mmol) of a 1.4M solution of potassium hexamethyldisilazide in tetrahydrofuran. This is allowed to stir for 1 hour when 8.0 g (43 mmol) of 8-carbomethoxyoctanal is added dropwise. The solution is stirred at −78° C. for 2 hours, allowed to warm to room temperature, and stirred for 2 days. The reaction is worked up by adding water and extracting three times with diethyl ether. The ether extracts are combined, washed with brine, dried over Na$_2$SO$_4$, filtered, and concentrated in vacuo to give a yellow solid. Pad filtration through flash silica gel eluting with 10% ethyl acetate/hexane, gives a yellow oil after concentration in vacuo. Flash chromatography on a 60 mm × 150 mm silica column eluting with 5% ethyl acetate/hexane gives 1.62 g (13%) of 10-(4-chlorophenyl)-dec-9-enoic acid methyl ester as a mixture of E and Z isomers.

To a solution of 1.62 g of 10-(4-chlorophenyl)-dec-9-enoic acid methyl ester in 200 mL of 4:1 methanol:water is added 5.4 g of KOH. The solution is stirred for 2 hours and extracted three times with diethyl ether. The aqueous layer is acidified with concentrated hydrochloric acid, and extracted three times with diethyl ether. The organic layers are combined, washed with brine, dried over Na$_2$SO$_4$, filtered, and concentrated in vacuo to give a yellow oil. The residue is purified via flash chromatography on a 40 mm × 150 mm silica column eluting with 40% ethyl acetate/hexane to give 1.6 g (100%) of pure 10-(4-chlorophenyl)dec-9-enoic acid as a mixture of E and Z isomers.

To a stirring solution of 189 mg (1.89 mmol) of tetronic acid in 15 mL of dimethylformamide is added 290 μL (2.08 mmol) of triethylamine and 8 mg (66 μmol) of 4-dimethylaminopyridine at 0° C. Next, 427 mg (2.22 mmol) of 1-(3-dimethylaminopropyl)-3-ethylcarbodiimide hydrochloride and 690 mg (2.20 mmol) of 10-(4-chlorophenyl)dec-9-enoic acid as a mixture of E and Z isomers are added and the reaction mixture is stirred overnight at room temperature. The reaction is acidified with 1.0N HCl and extracted three times with ethyl acetate. The combined organic layers are washed with brine, dried over Na$_2$SO$_4$, and concentrated in vacuo. The residue is purified via flash chromatography on a 40 mm × 150 mm silica gel column eluting with 5% methanol/ethyl acetate to give 400 mg (58%) of pure 4-hydroxy-3-[10-(4-chlorophenyl)-1-oxodec-9-enyl]-2(5H)-furanone as a mixture of E and Z isomers.

To a solution of 1.58 g (4.35 mmol) of 4-hydroxy-3-[10-(4-chlorophenyl)-1-oxodec-9-enyl]-2(5H)-furanone in 100 mL of ethyl acetate is added 250 mg of 5% palladium on carbon and subjected to atmospheric hydrogenation using a balloon to deliver the hydrogen. After 1.5 hours, the reaction is worked up by filtering through Solka Flok. The filtrate is washed with copious amounts of ethyl acetate and concentrated in vacuo to give 1.05 g (66%) of pure 4-hydroxy-3-[10-(4-chlorophenyl)1-oxodecyl]-2(5H)-furanone.

Spectral data follows: $^1$H NMR (CDCl$_3$, 400 MHz) δ7.22 (d, 2H, arom), 7.09 (d, 2H, arom), 4.66 (s, 2H, CH$_2$OC=O), 2.90 (t, 2H, J=7.5 Hz, O=CCH$_2$), 2.56 (t, 2H, CH$_2$Ar), 1.69 (m, 2H, CH$_2$), 1.57 (m, 2H, CH$_2$), 1.42-1.22 (m, 10H, CH$_2$); IR (KBr) 2920, 2840, 1760, (C=O), 1745, 1655, 1610 cm$^{-1}$; MS (EI) 364 (M+), 329, 155, 142, 125 (100).

Analysis Calc'd. for C$_{20}$H$_{25}$ClO$_4$: C, 65.84; H, 6.91. Found: C, 66.03; H, 7.02.

EXAMPLE 42

4-Hydroxy-3-[10-(3,4-dichlorophenyl)-1-oxodecyl]-2(5H)-furanone

Using the procedure of Example 41 for the synthesis of 4-hydroxy-3-[10-(4-chlorophenyl)-1-oxodecyl]-2(5H)-furanone above, but using 3,4-dichlorobenzyltriphenylphosphonium bromide in place of 4-chlorobenzyltriphenylphosphonium chloride, there is obtained the title compound.

Spectral data follows: $^1$H NMR (CDCl$_3$, 400 MHz) δ 7.29 (m, 2H, arom), 6.97 (m, 1H, arom), 4.64 (s, 2H, CH$_2$OC=O), 2.90 (t, 2H, J=7.5 Hz, O=CCH$_2$), 2.25 (t, 2H, CH$_2$Ar), 1.67 (m, 2H, CH$_2$), 1.54 (m, 2H, CH$_2$), 1.42-1.22 (m, 10H, CH$_2$); IR (KBr) 3180, 2920, 2845, 1760 (C=O), 1655, 1610 cm$^{-1}$; MS (EI) 398 (M+), 159, 127 (100).

Analysis Calc'd. for C$_{20}$H$_{24}$Cl$_2$O$_4$: C, 60.16; H, 6.06. Found: C, 60.55; H, 5.65.

EXAMPLE 43

4-Hydroxy-3-[10-[4-(1,1-dimethylethyl)phenyl]1-oxodecyl]-2(5H)-furanone

Using the procedure of Example 41, but using 4-(1,1-dimethylethyl)benzyltriphenylphosphonium bromide in place of 4-chlorobenzyltriphenylphosphonium chloride, there is obtained the title compound.

Spectral data follows: $^1$H NMR (CDCl$_3$, 400 MHz) δ 7.29 (d, 2H, arom), 7.11 (d, 2H, arom), 4.65 (s, 2H, CH$_2$OC=O), 2.92 (t, 2H, J=7.5 Hz, O=CCH$_2$), 2.57 (t, 2H, CH$_2$Ar), 1.70 (m, 2H, CH$_2$), 1.59 (m, 2H, CH$_2$), 1.42-1.22 (m, 10H, CH$_2$); IR (KBr) 3410, 2910, 2845, 1775 (C=O), 1695, 1650, 1605 cm$^{-1}$; MS (EI) 386 (M+), 371, 147, 127 (100).

Analysis Calc'd. for C$_{24}$H$_{34}$O$_4$: C, 74.58; H, 8.87. Found: C, 73.95; H, 8.67.

EXAMPLE 44

4-Hydroxy-3-[10-(4-bromophenyl)-1-oxodecyl]-2(5H)-furanone

Using the procedure of Example 41, but using 4-bromobenzyltriphenylphosphonium bromide in place of 4-chlorobenzyltriphenylphosphonium chloride, there is obtained the title compound.

Spectral data follows: $^1$H NMR (CDCl$_3$, 400 MNz) δ 7.37 (d, 2H, arom), 7.04 (d, 2H, arom), 4.64 (s, 2H, CH$_2$OC=O), 2.91 (t, 2H, J=7.5 Hz, O=CCH$_2$), 2.54 (t, 2H, CH$_2$Ar), 1.69 (m, 2H, CH$_2$), 1.59 (m, 2H, CH$_2$), 1.42-1.22 (m, 10H, CH$_2$); IR (KBr) 3200, 2930, 2850, 1765 (C=O), 1660, 1610 cm$^{-1}$; MS (CI+) 409 (MH+).

Analysis Calc'd. for C$_{20}$H$_{25}$BrO$_4$: C, 58.69; H, 6.16. Found: C, 59.24; H, 6.12.

EXAMPLE 45

4-Hydroxy-3[10-(4-trifluoromethyl)phenyl]-2(5H)-furanone

Using the procedure of Example 41, but using 4-trifluoromethylbenzyltriphenylphosphonium bromide in place of 4-chlorobenzyltriphenylphosphonium chloride, there is obtained the title compound.

Spectral data follows: $^1$H NMR (CDCl$_3$, 400 MHz) δ 7.52 (d, 2H, arom), 7.26 (d, 2H, arom), 4.63 (s, 2H, CH$_2$OC=O), 2.91 (t, 2H, J=7.5 Hz, O=CCH$_2$), 2.65 (t, 2H, CH$_2$Ar), 1.70 (m, 2H, CH$_2$), 1.61 (m, 2H, CH$_2$), 1.42-1.22 (m, 10H, CH$_2$); IR (KBr) 3400, 2920, 2840, 1770 (C=O), 1695, 1650, 1605 cm$^{-1}$; MS (neg. FAB) 397 (M-H).

Analysis Calc'd. for C$_{21}$H$_{25}$F$_3$O$_4$: C, 63.31; H, 6.32. Found: C, 62.97; H, 6.48.

EXAMPLE 46

4-Hydroxy-3[(Z,Z)-1-oxo-9,12-octadecadienyl]-2(5H)-thiophenone

To a stirring solution of 1.71 g (14.75 mmol) of thiotetronic acid in 10 mL of dimethylformamide is added 2.22 ML (17.2 mmol) of triethylamine and 592 mg (4.85 mmol) of 4-dimethylaminopyridine at 0° C. Next, 3.38 g (17.6 mmol) of 1-(3-dimethylaminopropyl)-3-ethylcarbodiimide hydrochloride and 4.96 g (17.7 mmol) of linoleic acid are added and the reaction mixture is stirred overnight at room temperature. The reaction is acidified with 1.0N HCl and extracted three times with diethyl ether. The combined organic layers are washed with brine, dried over Na$_2$SO$_4$, filtered, and concentrated in vacuo. The residue is recrystallized from pentane at −78° C. to give a solid which melts upon warming to room temperature giving 1.67 g (30%) of 4-hydroxy-3-[(Z,Z)-1-oxo-9,12-octadecadienyl]-2(5H)-thiophenone as an oil.

Spectral data follows: $^1$H NMR (CDCl$_3$, 400 MHz) δ 5.35 (m, 4H, CH$_2$CH=CHCH$_2$), 3.98 (s, 2H, CH$_2$SC=O), 2.95 (t, 2H, J=7.5 Hz, O=CCH$_2$), 2.77 (m, 2H, CH=CHCH$_2$CH=CH), 2.02 (m, 4H, CH$_2$CH=CH), 1.65 (m, 2H, CH$_2$), 1.42-1.22 (m, 14H, CH$_2$), 0.88 (t, 3H, J=7.5 Hz, CH$_3$); IR (Film) 2995, 2905, 2840, 1683 (C=O), 1612, 1565 cm$^{-1}$; MS (CI+) 379 (MH+), 281 (100), 263.

Analysis Calc'd. for C$_{22}$H$_{34}$SO$_3$: C, 69.80; H, 9.05. Found: C, 70.10; H, 9.28.

EXAMPLE 47

4-Hydroxy-3-[(Z)-1-oxo-9-octadecenyl]-2(5H)-thiophenone

To a stirring solution of 1.71 g (14.75 mmol) of thiotetronic acid in 10 mL of dimethylformamide is added 2.22 mL (17.2 mmol) of triethylamine and 592 mg (4.85 mmol) of 4-diemthylaminopyridine at 0° C. Next, 3.38 g (17.6 mmol) of 1-(3-dimethylaminopropyl)-3-ethylcarbodiimide hydrochloride and 5.0 g (17.7 mmol) of oleic acid are added and the reaction mixture is stirred overnight at room temperature. The reaction is acidified with 1.0N HCl and extracted three times with diethyl ether. The combined organic layers are washed with brine, dried over Na$_2$SO$_4$, filtered, and concentrated in vacuo. The residue is subjected to HPLC chromatography (2 inch Dynamax silica gel column, 25 mL/min) eluting with 100% ethyl acetate to give 1.85 g (33%) of 4-hydroxy-3-[(Z)-1-oxo-9-octadecenyl]-2(5H)-thiophenone as an oil.

Spectral data follows: $^1$H NMR (CDCl$_3$, 400 MHz) δ 5.34 (m, 2H, CH$_2$CH=CHCH$_2$), 3.98 (s, 2H, CH$_2$SC=O), 2.96 (t, 2H, J=7.5 Hz, O=CCH$_2$), 2.01 (m, 4H, CH$_2$CH=CH), 1.67 (m, 2H, CH$_2$), 1.42-1.20 (m, 20H, CH$_2$), 0.88 (t, 3H, J=7.5 Hz, CH$_3$); IR (Film) 2990, 2905, 2840, 1685 (C=O), 1615, 1565 cm$^{-1}$; MS (EI) 380 (M+), 362, 158 (100), 143, 116.

EXAMPLE 48

4-Hydroxy-3-[(Z)-1-oxo-9-tetra-decenyl]-2(5H)-thiophenone

To a stirring solution of 855 mg (7.37 mmol) of thiotetronic acid in 10 mL of dimethylformamide is added 902 μL (6.47 mmol) of triethylamine and 240 mg (1.96 mmol) of 4-dimethylaminopyridine at 0° C. Next, 1.68 g (8.76 mmol) of 1-(3-dimethylaminopropyl)-3-ethylcarbodiimide hydrochloride and 2.0 g (8.84 mmol) of myristoleic acid are added and the reaction mixture is stirred overnight at room temperature. The reaction is acidified with 1.0 N HCl and extracted three times with diethyl ether. The combined organic layers are washed with brine, dried over Na$_2$SO$_4$, filtered, and concentrated in vacuo. The residue is subjected to HPLC chromatography (2 inch Dynamax silica gel column, 25 mL/min) eluting with 100% ethyl acetate to give 785 mg (33%) of 4-hydroxy-3-[(Z)-1-oxo-9-tetradecenyl]-2(5H)-thiophenone as an oil.

Spectral data follows: $^1$H NMR (CDCl$_3$, 400 MHz) δ 5.35 (m, 2H, CH$_2$CH=CHCH$_2$), 3.98 (s, 2H, CH$_2$SC=O), 2.95 (t, 2H, J=7.5 Hz, O=CCH$_2$), 2.02 (m, 4H, CH$_2$CH=CH), 1.66 (m, 2H, CH$_2$), 1.31 (m, 12H, CH$_2$), 0.90 (t,3H, J=7.5 Hz, CH$_3$); IR (Film) 3020, 2920, 2860, 1695 (C=O), 1625, 1560 cm$^{-1}$; MS (EI) 324 (M+), 306, 157, 69 (100).

EXAMPLE 49

4-Hydroxy-3-[5-(4-chlorophenoxy)-1-oxopentyl]-2(5H)-thiophenone

To a stirring solution of 224 mg (1.89 mmol) of thiotetronic acid in 10 mL of dimethylformamide is added 290 μL (2.08 mmol) of triethylamine and 77 mg (631 μmol) of 4-dimethylaminopyridine at 0° C. Next, 440 mg (2.29 mmol) of 1-(3-dimethylaminopropyl)-3-ethylcarbodiimide hydrochloride and 530 mg (2.32 mmol) of 5-[4-(chlorophenoxy)]pentanoic acid are added and the reaction mixture is stirred overnight at room temperature. The reaction is acidified with 1.0N HCl and extracted three times with ether. The combined organic layers are dried over Na$_2$SO$_4$ and concentrated in vacuo giving a yellow solid. The residue is recrystallized from ethyl acetate/hexane at −78° C. to give 150 mg (24%) of 4-hydroxy-3-[5-(4-chlorophenoxy)-1-oxopentyl]-2(5H)-thiophenone.

Spectral data follows: $^1$H NMR (CDCl$_3$, 400 MHz) δ 7.20 (d, 2H, Ar), 6.79 (d, 2H, Ar), 3.95 (s, 2H, CH$_2$SC=O), 3.94 (t, 2H, CH$_2$OAr), 3.03 (t, 2H, O=CCH$_2$), 1.85 (m, 4H, CH$_2$); IR (KBr) 3410, 2960, 2940, 2880, 1680, 1625, 1580, 1490 cm$^{-1}$; MS (EI) 326 (M+), 199, 143, 128 (100).

Analysis Calc'd. for C$_{15}$H$_{15}$SO$_4$Cl: C, 55.13; H, 4.63, Found: C, 55.46; H, 4.78.

EXAMPLE 50

4-Hydroxy-3-[(Z,Z,Z)-1-oxo-6,9,12-octadecatrienyl]-2(5H)-thiophenone

To a stirring solution of 695 mg (6.04 mmol) of thiotetronic acid in 10 mL of dimethylformamide is added 902 μL (6.47 mmol) of triethylamine and 240 mg (1.97 mmol) of 4-dimethylaminopyridine at 0° C. Next, 1.37 g (7.13 mmol) of 1-(3-dimethylaminopropyl)-3-ethylcarbodiimide hydrochloride and 2.0 g (7.19 mmol) of γ-linolenic acid are added and the reaction mixture is stirred overnight at room temperature. The reaction is acidified with 1.0N HCl and extracted three times with diethyl ether. The combined organic layers are washed with brine, dried over Na$_2$SO$_4$, filtered, and concentrated in vacuo. The residue was subjected to HPLC chromatography (2 inch Dynamax silica gel column, 25 mL/min) eluting with 100% ethyl acetate to give 1.8 g (79%) of 4-hydroxy-3-[(Z,Z,Z)-1-oxo-6,9,12-octadecatrienyl]-2(5H)-thiophenone as an oil.

Spectral data follows: $^1$H NMR (CDCl$_3$, 400 MHz) δ 5.38 (m, 6H, CH$_2$CH=CHCH$_2$), 3.98 (s, 2H, CH$_2$SC=O), 2.97 (t, 2H, J=7.5 Hz, O=CCH$_2$), 2.81 (m, 4H, CH=CHCH$_2$CH=CH), 2.08 (m, 4H, CH$_2$CH=CH), 1.69 (m, 2H, CH$_2$), 1.47 (m, 2H, CH$_2$), 1.30 (m, 6H, CH$_2$), 0.88 (t, 3H, J=7.5 Hz, CH$_3$); IR (Film) 2980, 2900, 2820, 1695 (C=O), 1675, 1615, 1550 cm$^{-1}$; MS (CI+) 377 (MH+).

EXAMPLE 51

4-Hydroxy-3-[(Z)-1-oxo-6-octadecenyl]-2(5H)-thiophenone

To a stirring solution of 1.71 g (14.7 mmol) of thiotetronic acid in 20 mL of dimethylformamide is added 2.22 mL (15.9 mmol) of triethylamine and 592 mg (4.85 mmol) of 4-dimethylaminopyridine at 0° C. Next, 3.38 g (17.6 mmol) of 1-(3-dimethylaminopropyl)-3-ethylcarbodiimide hydrochloride and 5.0 g (17.7 mmol) of petroselinic acid are added and the reaction mixture is stirred overnight at room temperature. The reaction is acidified with 1.0N HCl and extracted three times with diethyl ether. The combined organic layers are washed with brine, dried over Na$_2$SO$_4$, filtered, and concentrated in vacuo. The residue is subjected to HPLC chromatography (2 inch Dynamax silica gel column, 25 mL/min) eluting with 100% ethyl acetate to give 1.2 g (21%) of 4-hydroxy-3-[(Z)-1-oxo-6-octadecenyl]-2(5H)-thiophenone as an oil.

Spectral data follows: $^1$H NMR (CDCl$_3$, 400 MHz) δ 5.34 (m, 2H, CH$_2$CH=CHCH$_2$), 3.98 (s, 2H, CH$_2$SC=O), 2.96 (t, 2H, J=7.5 Hz, O=CCH$_2$), 2.05 (m, 4H, CH$_2$CH=CHCH$_2$), 1.68 (m, 2H, CH$_2$), 1.43 (m, 2H, CH$_2$), 1.26 (m, 18H, CH$_2$), 0.88 (t, 3H, J=7.5 Hz, CH$_3$); IR (Film) 2980, 2900, 2820, 1695 (C=O), 1675, 1615 cm$^{-1}$; MS (CI+) 381 (MH+).

EXAMPLE 52

4-Hydroxy-3-[(Z)-8-(2-octylcyclopropyl)-1-oxooctyl]-2(5H)-thiophenone

To 2.2 g of zinc-copper couple in 30 mL of dry ether is added 5.7 mL (16.9 mmol) of methyl oleate and 5.4 mL (70.7 mmol) of diiodomethane. The reaction mixture is refluxed overnight, cooled to room temperature, poured into 1.0N HCl, and extracted three times with ether. The organic layers are combined, washed with brine, dried over MgSO$_4$, filtered, and concentrated in vacuo to give an oil. The oil is subjected to the conditions described in Example 51 above to give an oil free of starting material. The oil is taken up in a combination of tetrahydrofuran:methanol:water (2:1:1), followed by the addition of 4.0 g of 85% KOH. After 4 hours stirring at room temperature, the solvents are evaporated, the residue taken up in 0.1N KOH, and extracted three times with ether. The aqueous phase is acidified using concentrated HCl and extracted three times with ether. The ether layers are combined, washed with brine, dried over, MgSO$_4$, filtered, and concentrated in vacuo to give cis-8-(2-octylcyclopropyl) octanoic acid. Spectral data follows: $^1$H NMR (CDCl$_3$, 400 MHz) δ 2.35 (t, 2H, J=7.0 Hz, CH$_2$C=O), 0.6–1.7 (m, 33H).

To a stirring solution of 330 mg (2.84 mmol) of thiotetronic acid in 20 mL of dimethylformamide is added 410 μL (2.94 mmol) of triethylamine and 100 mg (820 μmol) of 4-dimethylaminopyridine at 0° C. Next, 640 mg (3.33 mmol) of 1-(3-dimethylaminopropyl)-3-ethylcarbodiimide hydrochloride and 1.0 g (3.38 mmol) of cis-8-(2-octylcyclopropyl)octanoic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue is recrystallized from 5% ethyl acetate/hexanes, filtering to give 250 mg (22%) of 4-hydroxy-3-[(Z)-8-(2-octylcyclopropyl)-1-oxooctyl]-2(5H)-thiophenone, mp 30°–32° C.

Spectral data follows: $^1$H NMR (CDCl$_3$, 400 MHz) δ 4.0 (s, 2H, CH$_2$SC=O), 2.96 (t, 2H, J=7.5 Hz, O=CCH$_2$), 1.65 (m, 2H, CH$_2$), 1.2–1.4 (m, 12H, aliphatic), 0.88 (t, 2H, J=7 Hz, cyclopropyl), 0.60 (m, 2H, cyclopropyl); IR (KBr) 2910, 2840, 1685 (C=O), 1620, 1570 cm$^{-1}$; MS (EI) 394 (M+).

Analysis Calc'd. for C$_{22}$H$_{38}$SO$_3$: C, 70.01; H, 9.71. Found: C, 70.13; H, 9.52.

EXAMPLE 53

4-Hydroxy-3-[(Z)-1-oxo-2-(2-pentylcyclopropy)ethyl]-2(5H)-furanone

Cis-nonen-1-ol (10.0 g) is subjected to the cyclopropanation conditions as described in the preparation of Example 52. The resulting residue is taken up in 100 mL of dichloromethane at 0° C., followed by the addition of 800 mg of sodium bromide in 2 mL of water and 150 mg of 2,2,6,6-tetramethyl-1-piperidinyloxy, free radical. To this mixture is added 1.50 g of Aliquot 336 followed by the dropwise addition of 9.2 g of sodium bicarbonate in 230 mL of 5% NaOCl. The aqueous phase is made basic, separated from the organic phase and acidified with concentrated HCl, and then extracted three times with dichloromethane. The combined organic layers are washed with water, dried over MgSO$_4$, and concentrated in vacuo to give cis-2-(2'-pentylcyclopropyl)acetic acid.

Spectral data follows: $^1$H NMR (CDCl$_3$, 400 MHz) δ 1.5 (m, 2H, CH$_2$C=O), 0.8–1.6 (m, 15H, aliphatic).

To a stirring solution of 500 mg (5.0 mmol) of tetronic acid in 20 mL of dimethylformamide is added 250 μL (1.79 mmol) of triethylamine and 200 mg (1.80 mmol) of 4-dimethylaminopyridine at 0° C. Next, 1.13 g (5.89 mmol) of 1-(3-dimethylaminopropyl)-3-ethylcarbodiimide hydrochloride and 1.0 g (5.89 mmol) of cis-2-(2'-pentylcyclopropyl)acetic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue is recrystallized from pentane, filtering to give 80 mg (6%) of 4-hydroxy-3-[(Z)-1-oxo-2-(2-pentylcyclopropyl)ethyl]-2(5H)-furanone, mp 55°–58° C.

Spectral data follows: $^1$H NMR (CDCl$_3$, 400 MHz) δ 4.67 (s, 2H, CH$_2$OC=O), 2.9 (m, 4H, CH$_2$cyclopropyl and O=CCH$_2$), 1.1–1.5 (m, 14H, aliphatic), 0.9 (m, 6H, CH$_3$ and cyclopropyl), 0.70 (m, 2H, cyclopropyl); IR (KBr) 2920, 2840, 1770 (C=O), 1650, 1610 cm$^{-1}$; MS (EI) 252 (M+).

Analysis Calc'd. for C$_{13}$H$_{20}$O$_4$: C, 66.65; H, 7.99. Found: C, 65.36; H, 7.27.

EXAMPLE 54

4-Hydroxy-3-[(Z)-8-(2-butylcyclopropyl)-1-oxooctyl]-2(5H)-furanone

Methyl myristoleate (1.5 g) is subjected to the cyclopropanation and saponification conditions described above for Example 52 to give cis-8-(2'-butylcyclopropyl)octanoic acid.

Spectral data follows: $^1$H NMR (CDCl$_3$, 400 MHz) δ 2.35 (t, 2H, J=7.5 Hz, CH$_2$C=O), 0.6–1.8 (m, 25H).

To a stirring solution of 300 mg (3.0 mmol) of tetronic acid in 20 mL of dimethylformamide is added 460 μL (3.21 mmol) of triethylamine and 700 mg (5.74 mmol) of 4-dimethylaminopyridine at 0° C. Next, 700 mg (3.65 mmol) of 1-(3-dimethylaminopropyl)-3-ethylcarbodiimide hydrochloride and 820 mg (3.42 mmol) of cis-8-(2'-butylcyclopropyl)octanoic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue was subjected to flash chromatography (acid washed silica gel) eluting with 50% ethyl acetate/hexanes to give 10 mg (10%) of 4-hydroxy-3-[(Z)-8-(2-butylcyclopropyl)-1-oxooctyl]-2(5H)-furanone as a yellow wax.

Spectral data follows: $^1$H NMR (CDCl$_3$, 400 MHz) δ 4.68 (s, 2H, CH$_2$OC=O), 2.92 (t, 2H, J=7.5 Hz, O=CCH$_2$), 0.60–2.0 (m, 15H,cyclopropyl and aliphatic); IR (KBr) 2920, 2850, 1780 (C=O), 1750, 1650, 1610 cm$^{-1}$; MS (EI) 322 (M+).

Analysis Calc'd. for C$_{19}$H$_{30}$O$_4$: C, 70.77; H, 9.38, Found: C, 70.06; H, 8.86.

EXAMPLE 55

4-Hydroxy-3-[(Z)-1-oxo-5-(2-undecylcyclopropyl)pentyl]-2(5H-furanone

Methyl petroselinate (2.5 g) was subjected to the cyclopropanation and saponification conditions described in Example 52 to give cis-5-(2'-undecylcyclopropyl)pentanoic acid.

Spectral data follows: $^1$H NMR (CDCl$_3$, 400 MHz) δ 2.35 (t, 2H, J=7 Hz, CH$_2$C=O), 0.6–1.8 (m, 33H, aliphatic).

To a stirring solution of 420 mg (4.20 mmol) of tetronic acid in 20 mL of dimethylformamide is added 640 μL (4.59 mmol) of triethylamine and 160 mg (1.31 mmol) of 4-dimethylaminopyridine at 0° C. Next, 1.0 g (5.20 mmol) of 1-(3-dimethylaminopropyl)-3-ethylcarbodiimide hydrochloride and 1.5 g (5.06 mmol) of cis-5-(2'-undecylcyclopropyl)pentanoic acid are added and the reaction mixture is stirred overnight at room temperature. The reaction is acidified with 1.0N HCl and extracted three times with ethyl acetate. The combined organic layers are washed with brine, dried over MgSO$_4$, and concentrated in vacuo. The residue is subjected to flash chromatography (acid washed silica gel) eluting with 50% ethyl acetate/hexanes to give a 400 mg (25%) of 4-hydroxy-3-[(Z)-1-oxo-5-(2-undecylcyclopropyl)pentyl]-2(5H)-furanone as a yellow solid, mp 40°–42° C.

Spectral data follows: $^1$H NMR (CDCl$_3$, 400 MHz) δ 4.68 (s, 2H, CH$_2$OC=O), 2.95 (t, 2H, J=7.5 Hz, O=CCH$_2$), 0.60–2.1 (m, 20H,cyclopropyl and aliphatic); IR (KBr) 2920, 2840, 1770 (C=O), 1690, 1600 cm$^{-1}$; MS (EI) 378 (M+).

Analysis Calc'd. for C$_{23}$H$_{38}$O$_4$: C, 72.98; H, 10.12. Found: C, 72.64; H, 8.88.

EXAMPLE 56

4-Hydroxy-3-[(Z)-1-oxo-2-(2-pentylcyclopropyl)ethyl]-2(5H)-thiophenone

Cis-nonen-1-ol (10.0 g) is subjected to the cyclopropanation conditions described in the preparation of Example 52. The resulting residue is taken up in 100 mL of dichloromethane at 0° C., followed by the addition of 800 mg of sodium bromide in 2 mL of water and 150 mg of 2,2,6,6-tetramethyl-1-piperidinyloxy, free radical. To this mixture is added 1.50 g of Aliquot 336 followed by the dropwise addition of 9.2 g of sodium bicarbonate in 230 mL of 5% NaOCl. The aqueous phase is made basic, separated from the organic phase and acidified with concentrated HCl, and then extracted three times with dichloromethane. The combined organic layers are washed with water, dried over $MgSO_4$, and concentrated in vacuo to give cis-2-(2'-pentylcyclopropyl)acetic acid.

Spectral data follows: $^1H$ NMR ($CDCl_3$, 400 MHz) δ 1.5 (m, 2H, $CH_2C=O$), 0.8–1.6 (m, 15H, aliphatic).

To a stirring solution of 2.0 g (17.2 mmol) of thiotetronic acid in 20 mL of dimethylformamide is added 2.6 mL (18.64 mmol) of triethylamine and 640 mg (5.25 mmol) of 4-dimethylaminopyridine at 0° C. Next, 4.0 g (20.8 mmol) of 1-(3-dimethylaminopropyl)-3-ethylcarbodiimide hydrochloride and 3.5 g (20.6 mmol) of cis-2-(2'-pentylcyclopropyl)acetic acid are added and the reaction mixture is stirred overnight at room temperature. The reaction is acidified with 1.0N HCl and extracted three times with ethyl acetate. The combined organic layers are washed with brine, dried over $MgSO_4$, and concentrated in vacuo. The residue is subjected to flash chromatography (acid washed silica gel) eluting with 10% ethyl acetate/hexanes to give 400 mg (9%) of 4-hydroxy-3-[(Z)-1-oxo-2-(2-pentylcyclopropyl)ethyl]-2(5H)-thiophenone as an orange oil.

Spectral data follows: $^1H$ NMR ($CDCl_3$, 400 MHz) δ 4.0 (s, 2H, $CH_2SC=O$), 3.0 (m, 4H, $CH_2$cyclopropyl and $O=CCH_2$), 1.65 (m, 2H, $CH_2$), 0.7–1.5 (m, 10H, aliphatic); IR (KBr) 2920, 1685 (C=O), 1620, 1570 $cm^{-1}$; MS (EI) 268 (M+).

Analysis Calc'd. for $C_{13}H_{20}SO_3$: C, 62.66; H, 7.51. Found: C, 62.84; H, 7.36.

EXAMPLE 57

4-Hydroxy-3-[1-oxohexadecyl]-2(5H)-furanone

To a stirring solution of 650 mg (6.5 mmol) of tetronic acid in 20 mL of dimethylformamide is added 1.0 mL (7.17 mmol) of triethylamine and 230 mg (1.88 mmol) of 4-dimethylaminopyridine at 0° C. Next, 1.50 g (7.81 mmol) of 1-(3-dimethylaminopropyl)-3-ethylcarbodiimide hydrochloride and 2.0 g (7.81 mmol) of palmitic acid are added and the reaction mixture is stirred overnight at room temperature. The reaction is acidified with 1.0N HCl and extracted three times with ethyl acetate. The combined organic layers are washed with brine, dried over $MgSO_4$, and concentrated in vacuo. The residue is recrystallized from pentane to give 2.0 g (91%) of 4-hydroxy-3-[1-oxohexadecyl]-2(5H)-furanone, mp 81°–83° C.

Spectral data follows: $^1H$ NMR ($CDCl_3$, 400 MHz) δ 4.7 (s, 2H, $CH_2OC=O$), 2.9 (t, 2H, J=7.0 Hz, $O=CCH_2$), 1.8–0.8 (m, 29H, aliphatic); IR (KBr) 2920, 2840, 1775 (C=O), 1750, 1660, 1620 $cm^{-1}$; MS (EI) 338 (M+).

Analysis Calc'd. for $C_{20}H_{34}O_4$: C, 70.97; H, 10.12. Found: C, 70.91; H, 9.73.

EXAMPLE 58

The compounds 5- and 12-hydroxyeicosatetraenoic acid (5-HETE and 12-HETE) and $LTB_4$ are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, J. Roy. Soc. Med., 74, 831 (1981)]. Compounds which inhibit the $PLA_2$-mediated release of arachidonic acid thereby effectively prevent the oxidation of arachidonic acid to the various leukotriene products via the lipoxygenase cascade. Accordingly, the specificity of action of $PLA_2$ inhibitors can be determined by the activity of test compounds in this assay, which measures the ability of compounds to inhibit the synthesis of $LTB_4$ and 5-HETE by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150–200 g) which receive an injection of 6% glycogen (10 ml i.p.). Rats are sacrificed 18–24 hours post injection by $CO_2$ asphyxiation and the elicited cells are harvested by peritoneal lavage using physiological saline (0.9% NaCl). The exudate is centrifuged at 400 xg for 10 minutes. The supernatant fluid is discarded and the cell pellet is resuspended to a concentration of $2.0 \times 10^7$ cells/mL in HBSS containing $Ca^{++}$ and $Mg^{++}$ and 10 μM L-cysteine.

To 1 mL aliquots of cell suspension, test drugs or vehicle are added, then preincubated at 37° C. for 10 minutes. A23187 (1 μM), [$^3H$]-AA (3.0 μCi/mL) and unlabeled AA (1 μM) are then added and the samples are further incubated for 10 minutes. The reaction is terminated by centrifugation and pelleting cells. Supernatants are then analyzed by HPLC analysis on a 15 cm×4.6 mm ID supelcosil LC-18 (Supelco)(3M) column, using a two solvent system at a flow rate of 1.4 mL total flow as follows:

Solvent A: 70:30 17.4 mM $H_3PO_4$:$CH_3CN$.
Solvent B: $CH_3CN$.

| Gradient: (system is equilibrated with Solvent A) | | |
|---|---|---|
| Time | Percent A | Percent B |
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.

Injections: 140 μL of each supernatant is injected directly onto column and $^3H$ arachidonic acid metabolites are monitored using an on-line radioactivity detector (Ramona, IN/US, Fairfield, N.J.).

Standards: $10^4$–$2.0 \times 10^4$ dpm of eicosanoids of interest are injected in 90 μL EtOH cocktail.

Co-chromatography with standard [$^3H$] leukotriene $B_4$ ($LTB_4$) in medium of stimulated PMN exposed to drug is compared to that found in medium of stimulated cells exposed to no drug, generating percent inhibition.

Results are expressed as percent inhibition at a given compound dose or as an $IC_{50}$ value.

Testing compounds of the invention in this assay gave the following results:

TABLE I

| Compound of | % Inhibition | |
|---|---|---|
| Example No. | $LTB_4$ | 5-HETE |
| etodolac | 21 (at 0.5 μM) | |
| indomethacin | 31 (at 10 μM) | |
| 1 | 60 (at 50 μM) | |
| 7 | +13* (at 10 μM) | |
| 8 | +10* (at 10 μM) | |
| 9 | 1 (at 10 μM) | |
| 12 | +5* (at 10 μM) | |
| 23 | 83 (at 10 μM) | 93 (at 10 μM) |
| 25 | 8 (at 10 μM) | +81* (at 10 μM) |

TABLE I-continued

| Compound of Example No. | % Inhibition | |
|---|---|---|
| | LTB$_4$ | 5-HETE |
| 26 | 82 (at 10 μM) | 85 (at 10 μM) |

*Denotes potentiation of lipoxygenase (LTB$_4$ or 5-HETE synthesis).

EXAMPLE 59

The procedure of Example 58 is also employed for the determination of the extent to which compounds of the invention inhibit the synthesis of the arachidonic acid cyclooxygenase oxidation products PGE$_2$ and TxB$_2$.

In this assay, the procedure of Example 58 is carried out as described. However, in order to determine cyclooxygenase activity, the samples are co-chromatographed with authentic reference [$^3$H]-TxB$_2$ or [$^3$H]-PGE$_2$.

The results are calculated as in Example 58 and presented below:

TABLE II

| Compound of Example No. | % Inhibition | |
|---|---|---|
| | TxB$_2$ | PGE$_2$ |
| etodolac | 100 (at 0.5 μM) | |
| indomethacin | 100 (at 10 μM) | |
| 1 | 71 (at 50 μM) | |
| 7 | +18* (at 10 μM) | |
| 8 | 1 (at 10 μM) | |
| 9 | 31 (at 10 μM) | |
| 12 | 9 (at 10 μM) | |
| 23 | 8 (at 10 μM) | +1* (at 10 μM) |
| 25 | +8* (at 10 μM) | +68* (at 10 μM) |
| 26 | 1 (at 10 μM) | +6* (at 10 μM) |

*Denotes a potentiation of cyclooxygenase (PGE$_2$ or TxB$_2$ synthesis).

EXAMPLE 60

The compounds of the invention are tested in an in vitro phospholipase A$_2$ assay to determine the ability of the compounds to inhibit the biosynthesis of platelet-activating factor and LTB$_4$ in purified human neutrophils.

This assay is carried out as follows:

Isolation of Human Polymorphonuclear Neutrophils

A leukocyte enriched blood sample obtained from a healthy male donor is procured by leukophoresis using a Haemonetics model 30+ blood processor (Biological Specialties, Inc., Lansdale, Penn.). The top "platelet-rich" layer is removed after a low speed spin (35 xg, 15 min, 25° C.) of the sample. The remaining cell suspension is centrifuged (400 xg, 10 min, 25° C.) to sediment the remaining cells. The supernatant is discarded and the cell pellet resuspended in 120 ml HBSS (without Ca$^{++}$/Mg$^{++}$). The cell suspension is subjected to ficoll-hypaque sedimentation (Histopaque 1077, 400 xg, 30 min, 25° C.). Contaminating erythrocytes are lysed by hypotonic shock (1 min). The cells are then washed once with 40 ml of HBSS and resuspended with HBSS (without Ca$^{++}$/Mg$^{++}$) to a concentration of 2.5×10$^7$ cells/ml for further use. Greater than 95% purity is obtained, as assessed by microscopic examination.

Platelet-Activating Factor Biosynthesis in Human Polymorphonuclear Neutrophils (PMN)

One ml of human PMN (2.5×10$^7$ cells/ml) is incubated with vehicle or drugs (10 μl) for 10 minutes at 30° C. After preincubation, an equal volume of HBSS (1 ml) containing 2.4 mM CaCl$_2$, 6 μM calcium ionophore A23187 and 50 μCi [$^3$H]-acetate is then incubated at 30° C. for 15 minutes. An aliquot (100 μl) of the reaction mixture is taken out and mixed with 900 μl of 15% ethanol. LTB$_4$ is extracted by using solid phase extraction on reverse phase C$_{18}$ columns to remove excess [$^3$H]-acetate and PAD. The C$_{18}$ column is prewashed once with 2 ml of ethanol and water. The sample aliquot is acidified with 0.1N HCl to pH 3 before applying to the column. The column is then washed with 2 ml of water followed by 2 ml of 15% ethanol and 2 ml of petroleum ether to remove excess labeled acetate. The sample is eluted with 2 ml of ethyl acetate. The collected samples are dried with nitrogen and resuspended in 0.5 ml RIA buffer. The quantity of LTB$_4$ in the sample is obtained from RIA determination. For PAF determination, the reaction is terminated by addition of 5 ml chloroform:methanol:acetic acid (2:1:0.04, v/v/v). [$^3$H]-PAF is obtained by Bligh and Dyer extraction. The chloroform phase is removed and dried under nitrogen. The residue is redissolved in 75 μl of chloroform:methanol (80:20, v/v). [$^3$H]-PAF is resolved from other phospholipids by TLC on RPC$_{18}$ plates with a solvent system of chloroform:methanol:water (2:3:1, v/v/v) and is quantitated using a Berthold automated TLC linear analyzer.

Data presented are the mean +/− s.d. of the values relative to control A23187 stimulated cells for each experiment assayed in triplicate. Percent inhibition when used is calculated as:

% Inhibition = 100 − [(x ÷ Control) × 100].

Dose response analysis is performed by non-linear regression analysis for curve fitting and IC$_{50}$ determination.

In this assay, scalaradial, an irreversible inhibitor of PLA$_2$, isolated from the marine sponge Cacospongia sp. gives an IC$_{50}$ of 1.0 μM.

When tested in this assay, the compounds of the invention gave the following results:

TABLE III

| Compound of Example No. | Dose, μM | % Inhibition PAF | Dose, μM | % Inhibition LTB$_4$ |
|---|---|---|---|---|
| 1 | 10 | 13 | 10 | 37 |
| | 25 | 32 | 25 | 46 |
| | 50 | 68 | | |
| 9 | 50 | 56 | 50 | 100 |
| 14 | 10 | 16 | 10 | 30 |
| | 25 | 19 | 25 | −5 |
| | 50 | 64 | | |
| 15 | 50 | 21 | 50 | 68 |
| 18 | 25 | 53 | 25 | 83 |
| | 50 | 47 | | |
| 20 | 50 | 83 | 50 | 95 |
| 22 | 10 | 24 | 10 | 93 |
| | 25 | 49 | 25 | 91 |
| | 50 | 67 | | |
| 25 | | | 10 | 74 |
| | 50 | 47 | 50 | 97 |
| 35 | | | 10 | 81.6 |
| | 50 | 5 | 50 | 98.5 |
| 46 | 25 | 7 | | |
| | 50 | 50 | 50 | 39 |
| 47 | 50 | 35 | 50 | 47 |
| 48 | 25 | 76 | 25 | 86 |
| 50 | 10 | 42 | | |
| | | | 25 | 100 |
| 51 | 50 | 70 | | |

EXAMPLE 61

The compounds of the invention are tested in an in vitro isolated phospholipase $A_2$ assay to determine the ability of the test compounds to inhibit the release of arachidonic acid from an arachidonic acid-containing substrate by the action of phospholipase $A_2$ enzyme from human and non-human sources.

This assay is carried out as follows:

Into a 15 mL polypropylene tube are added the following:

| Agent | Volume, μL | Final Conc. |
|---|---|---|
| $^3$H-AA *E. coli* substrate[1] | 25 | 5 nmoles PL |
| $CaCl_2$ (0.1 M)[2] | 5 | 5 mM |
| Tris-HCl (0.5 M) pH 7.5[3] | 20 | 100 mM |
| Water[4] | 25 | |
| Drug/vehicle[5] | 1 | 50 μM |
| $PLA_2$ | 25 | Volume yielding 12% hydrolysis in 10 min. |
| | 100 | |

*pre-incubate at room temperature 30 min prior to substrate addition.
[1] Prepared by adding 2 mL deionized and distilled water to 2 mL $^3$H-arachidonate labeled *E. coli* (lower count), to which is added to 1 mL of $^3$H-arachidonate labeled *E. coli* (higher count) to yield a total of 5 m substrate (containing 1000 nmoles phospholipid).
[2] Stock 0.1 m $CaCl_2$, required for enzyme activity.
[3] Stock 0.5 m Trisma-Base. Stock 0.5 M Trisma-HCl. Adjust pH to 7.5 (optimum for enzyme).
[4] Deionized and distilled water.
[5] Stock 10 mM prepared in dimethyl sulfoxide. Make 1:2 dilution with dimethyl sulfoxide and add 1 μL to 100 μL assay tube.
[6] Two human $PLA_2$ enzymes are used: a) Semi-purified human platelet acid extract $PLA_2$ (in 10 mM sodium acetate buffer, pH 4.5). Remove protein precipitate by centrifugation at about 2200 rpm for 10 minutes. b) Purified human synovial fluid.

Incubate the 100 μL reaction mixture for 10 minutes at 37° C. in a shaking water bath. The reaction is terminated by the addition of 2 mL tetrahydrofuran, followed by vortexing. $NH_2$ columns (100 μg/mL—Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by β-counting analysis. A "total counts" sample is prepared by pipetting 25 μL $^3$H-arachidonate *E. coli* directly into a scintillation vial to which is added 1 mL tetrahydrofuran. 10 mL aquasol (scintillation cocktail) is added to all samples.

Calculations:

$$\% \text{ hydrolysis} = \frac{[3H]AA \text{ dpm (sample)} - [3H]AA \text{ dpm (nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| | $IC_{50}$ (μM) | |
|---|---|---|
| Drug | Human Platelet $PLA_2$ | Human Synovial $PLA_2$ |
| Arachidonic Acid | 8.6 | 3.2 |
| Monoalide | 25.2 | 0.14 |

When tested in this assay, the compounds of the invention gave the following results:

TABLE IV

| Compound of Example No. | % Inhibition at 10 μM HP* | % Inhibition at 10 μM HSF** | $IC_{50}$ (μM) HP | $IC_{50}$ (μM) HSF |
|---|---|---|---|---|
| sulindac | 33 | 34 | | 30.2 |
| 1 | 14.9 | 35.1 | | 10.8 |
| 2 | 8 (at 50 μM) | 27 (at 50 μM) | | |
| 3 | 3.5 (at 50 μM) | 25 (at 50 μM) | | |
| 4 | 10 (at 50 μM) | 25 (at 50 μM) | | |
| 5 | 0 (at 50 μM) | 11 (at 50 μM) | | |
| 6 | 0 | 59 | | 8.7 |
| 7 | 0 | 98 | | 1.8 |
| 8 | 3 | 77 | | 10.5 |
| 9 | +18.5 | 97.3 | | 1.1 |
| 10 | +9.6 | 34 | | |
| 11 | 6.7 | 32 | | |
| 12 | +11 | 82 | | 2.0 |
| 13 | 11 | 34 | | |
| 14 | 44 | 95 | 1.7 | 0.48 |
| 15 | 30 | 77.5 | | |
| 16 | +2.1 | 5.5 | | |
| 17 | 16 | 9 | | |
| 18 | 46 | 9 | | |
| 19 | 83 | 88 | | |
| 20 | 62 | 81 | | |
| 21 | 2.5 | 24 | | |
| 22 | 71 | 89.8 | 13.1 | 2.5 |
| 23 | 52.7 | 44 | | |
| 24A | 45.4 | 80.7 | | |
| 24 | 56.6 | 79.5 | | |
| 25 | 58.3 | 28.8 | 26.7 | 33.4 |
| 26 | 24.4 | +1.7 | | |
| 27 | 34.9 | +31.2 | | |
| 28 | 37.4 | 12.6 | | |
| 29 | 20.6 | 33.6 | | |
| 30 | 37.4 | 21.0 | | |
| 31A | 47.7 | 43.2 | | |
| 31 | 33.5 | 34.5 | | |
| 32 | 31.6 | 15.1 | | |
| 33 | 37.1 | +10.0 | | |
| 35 | 68.6 | 28.4 | 7.5 | 16 |
| 36 | 25.4 | 10.3 | | |
| 37 | 22.5 | +35.7 | | |
| 38 | 80.9 | 18.8 | | |
| 39 | 24.4 | +20.3 | | |
| 40A | 87.7 | 74.2 | | |
| 40 | 96.5 | 91.0 | | |
| 41 | 12 | 13 | | |
| 42 | 6.6 | 22 | | |
| 43 | 29.7 | 44.4 | | |
| 44 | 16.1 | 37.0 | | |
| 45 | 63.0 | 55.6 | | |
| 46 | 16.4 | 72.0 | | |
| 47 | 13.8 | 34.8 | | |
| 48 | 1.1 | 50.9 | | |
| 49 | 1.7 | 6.7 | | |
| 50 | 14.1 | 55.9 | | |
| 51 | 15.2 | 29.4 | | |
| 52 | 8.4 | 18.6 | | |
| 53 | 1.7 | 0.1 | | |

*human platelet
**human synovial fluid

EXAMPLE 62

The ability of the compounds of the invention to act as inhibitors of the enzymes 5-lipoxygenase and cyclooxygenase is measured in the resident murine peritoneal macrophage assay.

This assay is carried out as follows:

Resident peritoneal macrophages are collected from female Swiss Webster mice (49 days old, 20–25 gms, Buckshire) by lavaging with 7–8 ml Hanks Balanced Salt Solution (HBSS) without $Ca^{++}$ and $Mg^{++}$ (GIBCO). The lavage fluid from several mice is pooled and centrifuged at 4° C. for 10 minutes at 400 xg. The cell pellet is resuspended in Medium 199 (GIBCO) with HEPES buffer containing 100 μg/ml gentamicin. Two ml of the cell suspension ($4 \times 10^6$ cells) are then plated on 35 mm culture dishes (Nunc).

A macrophage monolayer is established after a 1-1.5 hour incubation of the cells at 37° C. in an atmosphere of 95% $O_2$ and 5% $CO_2$. The monolayers are washed 2× with 2 ml HBDSS, containing $Ca^{++}$ and $Mg^{++}$ after which 2 ml Medium 199 supplemented with 10% freshly thawed heat-inactivated fetal bovine serum and 100 µg/ml gentamicin is added for an overnight incubation.

Residual serum and cellular debris are removed from the monolayers by washing 3× with 2 ml HBSS containing $Ca^{++}$ and $Mg^{++}$. Macrophages are preincubated for 5 minutes with 1 ml serum-free M199 containing 10 µl dimethyl sulfoxide (DMSO) vehicle or test compound prior to cell activation with zymosan (100 Mg/ml) or arachidonic acid (AA) (2 µM). After 2 hours, the supernatants are removed and either assayed for $LTC_4$ and $PGE_2$ by radioimmunoassay (RIA) directly or stored at −20° C. In all cases, results are expressed as ng metabolite/$4 \times 10^6$ cells.

| Metabolite | Range of detection (µg/ml) | Metabolite Levels (ng/4 × $10^6$ cells) (x ± S.E.M., n) |
|---|---|---|
| $LTC_4$ | 0.25-16 | 93.7 ± 9.9 (34) |
| $PGE_2$ | 0.027-20 | 30.90 ± 1.93 (39) |

Summary of RIAs used for quantitation of metabolite levels in zymosan or arachidonic acid stimulated mouse macrophage culture media.

Calculations

Raw data (dpm) may be stored directly onto an "Autostart" tape using the HP85 in room C-096. The raw data are converted to ng metabolite/$4-10^6$ cells using the standard curve by a "RIANAL" program (HP85) or a "NONLIN" program (HP9816). Results are then expressed as percent inhibition of zymosan induced, leukotriene or prostaglandin synthesis (control) using the equation:

$$\% \text{ Inhibition} = \frac{\text{control metabolite level} - \text{sample metabolite level}}{\text{control metabolite level}} \times 100$$

REFERENCE COMPOUNDS

The compounds used are listed below.

$IC_{50}$ values of reference 5-lipoxygenase and/or cyclooxygenase inhibitors.

| Compound | $IC_{50}$ µM (95% Confidence limits) | |
|---|---|---|
|  | $LTC_4$ | $PGE_2$ |
| BW 755c | 0.21 | 1.04 |
|  | (0.10, 0.42) | (0.73, 1.49) |
| ETYA | 0.44 | 1.26 |
|  | (0.36, 0.53) | (0.99, 1.60) |
| Indomethacin | >50 | 0.002 |
|  |  | (0.001, 0.003) |
| NDGA | 1.87 | 2.15 |
|  | (0.22, 15.57) | (1.15, 4.04) |

When tested in this assay, the compounds of the invention exhibited the following levels of enzyme inhibition:

TABLE V

| Compound of Example No. | $PGE_2$ | | | | | $LTC_4$ | | | | |
|---|---|---|---|---|---|---|---|---|---|---|
|  | zymosan | | | AA | | zymosan | | | AA | |
|  | Dose µM | % Inhibition | $IC_{50}$ | Dose µM | % Inhibition | Dose µM | % Inhibition | $IC_{50}$ | Dose µM | % Inhibition |
| 1 |  |  | 3.0 |  |  |  |  | 2.0 |  |  |
| 9 |  |  | 0.2 | 0.3 | 4 |  |  | 0.2 | 0.3 | 8 |
| 14 |  |  | 4.0 | 5 | 38 |  |  |  | 5 | 61 |
| 15 |  |  | 0.35 |  |  |  |  | 0.45 |  |  |
| 22 |  |  | 0.2 |  |  |  |  | 0.2 |  |  |
| 18 |  |  | 0.14 | 0.3 | −17 |  |  | 0.16 | 0.3 | −6 |
| 25 |  |  | 0.2 | 0.6 | −338 |  |  | 0.25 | 0.6 | −4 |
| 19 | 0.5 | 68.4 |  |  |  | 0.5 | 37.5 |  |  |  |
| 20 |  |  | 0.7 | 1.0 | 1 |  |  | 0.7 | 1.0 | −51 |
| 30 | 1.0 | 45.8 |  |  |  | 1.0 | 41.5 |  |  |  |
| 35 |  |  | 0.15 |  |  |  |  | 0.3 |  |  |
| 38 | 1.0 | 75.8 |  |  |  | 1.0 | 46.4 |  |  |  |
| 40 |  | 37 | 0.8 |  |  |  | 87 | 0.8 |  |  |
| 41 | 0.1 | 29 |  |  |  | 0.1 | 61 |  |  |  |
|  | 0.5 | 97 |  |  |  | 0.5 | 90 |  |  |  |
| 42 | 0.1 | −8 |  |  |  | 0.1 | 58 |  |  |  |
|  | 0.5 | 97 |  |  |  | 0.5 | 70 |  |  |  |
| 43 | 0.1 | 54 |  |  |  | 0.1 | 71 |  |  |  |
|  | 0.5 | 92 |  |  |  | 0.5 | 96 |  |  |  |
| 44 | 0.1 | −20 |  |  |  | 0.1 | 58 |  |  |  |
|  | 0.5 | 88 |  |  |  | 0.5 | 94 |  |  |  |
| 45 | 0.2 | 45 |  |  |  | 0.2 | 34.5 |  |  |  |
| 46 | 0.1 | 51.9 | 0.1 | 0.5 | 5 |  |  | 0.3 | 0.5 | −9 |
| 47 | 0.1 | 48.4 | 0.1 | 0.3 | −26 | 0.1 | 46.2 | 0.1 | 0.3 | 9 |
| 48 | 0.1 | 71.8 |  | 0.3 | −16 | 0.1 | 25.3 |  | 0.3 | −5 |
|  | 0.03 | 25.4 |  |  |  | 1.0 | 77.1 |  |  |  |
| 49 | 0.5 | −11.8 |  |  |  | 0.5 | −19.7 |  |  |  |
| 50 | 0.1 | 21.6 |  | 0.5 | −35 | 0.1 | 38.8 |  | 0.5 | −33 |
|  | 0.5 | 70.1 |  |  |  | 0.5 | 48.1 |  |  |  |
| 51 | 0.1 | 0.5 |  | 0.5 | −795 | 0.1 | 21.1 |  | 0.5 | −4 |
|  | 0.5 | 91.3 |  |  |  | 0.5 | 59.4 |  |  |  |
| 54 | 0.1 | 49.5 |  |  |  | 0.1 | 59.3 |  |  |  |
| 55 | 0.1 | 39.2 |  |  |  | 0.1 | 80.3 |  |  |  |
|  | 0.5 | 74.3 |  |  |  | 0.5 | 64.2 |  |  |  |

EXAMPLE 63

The ability of the compounds of the invention to inhibit paw edema induced by the exogenous administration of $PLA_2$ is measured in the in vivo $PLA_2$ murine paw edema assay.

The assay is carried out as follows:

Non-fasted, male CD-1 mice (8 weeks old; 31–36 grams) are placed in plastic boxes in groups of six. The right hind paw volume is measured using mercury plethysmography (zero time). Compounds are dosed orally (0.5 mL of 0.5% Tween-80) 1 or 3 hours prior to $PLA_2$ injection or intravenously (0.2 mL in 0.3% dimethylsulfoxide/saline) 3 minutes prior to $PLA_2$ injection. A solution of purified $PLA_2$, from the diamond back cotton mouth snake (*A. piscivorus piscivorus*) is prepared in saline at a concentration of 6 μg/mL. Fifty (50) μL (0.3 μg) of this $PLA_2$ solution is injected subcutaneously into the right hind paw with a plastic 1 mL plastic syringe (27 gauge, 1" needle). Paw volume of the injected paw is measured again at 10 minutes, 30 minutes and 60 minutes after $PLA_2$ injection. Animals are euthanized with $CO_2$ at the completion of the study.

The paw edema is calculated by subtracting the zero time volume from the volume recorded at each time period. Mean paw edema for each treatment group is then calculated and expressed as (μL±S.E.). Drug effects are expressed as a percent change from control (vehicle) values. Statistical significance is determined by a one-way analysis of variance with LSD comparison to control (p<0.05). $ED_{50}$'s are determined using repression analysis.

The activity of standard drugs in this assay is as follows:

| Compound | $ED_{50}$ mg/kg p.o. at +10 min. |
|---|---|
| Cyproheptadine | 3.1 |
| BW755C | 50 |
| Dexamethasone* | 10 |
| Naproxen | 18 |
| Aristolochic Acid** | Not Active |
| Luffarrellolide** | Not Active |

*p.o. - 3 hr.
**Some activity (30% inhibition) only when co-injected with enzyme.

When tested in this assay, the compounds of the invention gave the following results:

TABLE VI

| Compound of Example No. | Dose mg/kg | % Change in Edema 10 min | 30 min | 60 min |
|---|---|---|---|---|
| indomethacin | 10 (p.o.)** | −32 | −31 | −42 |
| 1 | 10 (i.v.)* | −51 | −43 | −23 |
|  | 100 (p.o.) | −36 | −29 | −29 |
| 7 | 10 (i.v.) | −19 | +39 | +15 |
|  | 100 (p.o.) | −24 | −4 | −9 |
| 9 | 10 (i.v.) | −48 | −42 | −48 |
|  | 100 (p.o.) | −1 | +1.5 | +7.1 |
| 12 | 10 (i.v.) | −11 | −19 | +24 |
|  | 100 (p.o.) | −27 | −33 | −2 |
| 23 | 1 (i.p.)*** | — | −41 | −20 |
|  | 10 (i.p.) | — | −48 | −28 |
| 25 | 1 (i.p.) | −50 | −65 | −1 |
|  | 10 (i.p.) | −38 | −44 | −18 |
|  | 200 (p.o.) | −40 | −33 | −43 |
| 26 | 1 (i.p.) | — | −62 | −38 |
|  | 10 (i.p.) | — | −67 | −43 |

*intravenous
**peroral
***intraperitoneal

The results show that the compounds of the invention are effective in vivo in inhibiting edema induced by the exogenous administration of snake venom $PLA_2$.

EXAMPLE 64

The compounds of the invention are evaluated for their ability to inhibit the lipoxygenase and/or cyclooxygenase pathways of arachidonic acid metabolism in the in vivo murine zymosan peritonitis assay.

This assay is carried out as follows:

Male CD-1 mice (8 weeks old) are placed in plastic boxes in groups of six. Animals are injected with 1 mL i.p. of either 1% zymosan in pyrogen free 0.9% saline or saline (unstimulated control). Compounds are dosed orally 1 hour prior to zymosan injection. Twenty minutes after zymosan injection, the mice are asphyxiated by $CO_2$ inhalation and the peritoneal cavity is lavaged with 2 mL ice cold Hanks Balanced Salt Solution (HBSS) without $CaCl_2$, $MgSO_4$. $7H_2O$ and $MgCl_2.6H_2O$. Peritoneal lavage fluid from each mouse is removed by syringe and placed in 5 mL plastic test tubes put on ice and volume is noted. Preparation of samples for evaluation by ELISA is as follows: Samples are centrifuged at 800 xg for 15 minutes; 1 mL of the supernatant is added to 8 mL ice cold methanol and kept at −70° C. overnight to precipitate protein; and samples are then centrifuged at 800 xg for 15 minutes, followed by a drying procedure in a Savant speed vac concentrator. The samples are reconstituted with 1 mL ice cold ELISA buffer and stored at −70° C. until assayed. The assay for eicosanoids ($LTC_4$ and 6-keto-$PGF_{1\alpha}$) is performed according to conventional ELISA procedures.

Compounds to be tested orally are suspended in 0.5% Tween 80. Compounds to be tested intraperitoneally are suspended in 0.5% methylcellulose in 0.9% saline.

The total metabolite level in lavage fluid/mouse is calculated and the significance is determined by a one-way analysis of variance with LSD comparisons to control (p≦0.05). Drug effects are expressed as a percent change from control values.

The activity of standard drugs in this assay is as follows:

| Compound | $ED_{50}$ mg/kg p.o. $LTC_4$ | 6-keto-$PGF_{1\alpha}/TxB_2$ |
|---|---|---|
| BW755C | <10 | 22.0 |
| Phenidone | 24.0 | <30.0 |
| Indomethacin | Not Active | 0.126 |
| Ibuprofen | Not Active | 7.0 |

When tested in this assay a compound of the invention and the anti-inflammatory compound etodolac gave the following results:

TABLE VII

| Compound of Example No. | Dose mg/kg | % Inhibition $LTC_4$ | 6-keto-PGF |
|---|---|---|---|
| indomethacin | 10 (p.o.)* | +25 |  |
| 1 | 100 (p.o.) | −58 | −58** |

*perorally administered
**negative values denote potentiation

EXAMPLE 65

The ability of the compounds of the invention to inhibit inflammatory responses is examined in the in vivo arachidonic acid (AA)/12-o-tetradecanoylphorbol acetate (TPA)-induced murine ear edema assay.

This assay is carried out as follows:

Swiss Webster female mice (Buckshire), approximately 8 weeks old are placed into plastic boxes in groups of six. Eight groups of mice receive AA topically on the right ear, and another 8 groups receive TPA topically on the right ear. AA and TPA are dissolved in acetone at concentrations of 100 mg/ml and 100 µg/ml respectively. The phlogistics are applied to the right ear by the means of an automatic pipet. Volumes of 10 µl are applied to the inner and outer surfaces of the ear. Each mouse receives either 2 mg/ear AA or 2 µg/ear TPA. The left ear (control) receives acetone delivered in the same manner. Topical and subcutaneous dosing regimens are as follows 1) drugs are given 30 minutes prior to AA treatment and 2) drugs are given 30 minutes after treatment with TPA.

Measurements are taken with Oditest calipers, 0–10 mm with 0.01 graduations. The right and left ears are measured after 1 hr AA-induced inflammation and 4 hours after TPA-induced inflammation.

Calculations

The difference between right and left ear thickness is calculated and the significance is determined by a one way analysis of variance with Dunnett's comparisons to control (P=0.05). Drug effects are expressed as a percent change from control values:

$$\% \text{ change from control} = \frac{(\text{Rt. ear} - \text{Lt. ear})\text{drug} - (\text{Rt. ear} - \text{Lt. ear})\text{control}}{(\text{Rt. ear} - \text{Lt. ear})\text{control}} \times 100$$

Activity of standard drugs:

| Drug | Oral ED$_{50}$ (mg/kg) | |
|---|---|---|
| | (AA) | (TPA) |
| BW755c | 65 | 88 |
| Phenidone | 85 | 235 |
| Indomethacin | inactive at 10 | inactive at 10 |

The results for compounds of the invention tested in this assay are presented in Table VIII.

TABLE VIII

| | | TPA - Route of Drug Administration | | | |
|---|---|---|---|---|---|
| Compound of Example No. | | Topical | | Subcutaneous | |
| | vehicle | % Inhibition at 200 µg | IC$_{50}$ | % Inhibition at 50 m/kg | ED$_{50}$ mg/kg |
| 1 | acetone | 31 | 250 | 23 | |
| 9 | acetone | 42 | 190 | 7 | |
|   | EPW | 56 | | 28 | |
| 14 | acetone | 28 | 150 | 21 | 118 |
|   | EPW | 51 | | 37 | |
| 15 | acetone | 34 | | | |
| 18 | acetone | 1 | | 37 | |
|   | EPW | 53 | | 28 | |
| 22 | acetone | 40 | 450 | 36 | |
| 25 | acetone | 30 | | 64 | |
|   |   | 86 | | | |
| 20 | acetone | 80 | 160 | 76 | 31 |
|   | EPW | 81 | | | |
| 35 | acetone | 39 | | | |
| 38 | acetone | 23 | | | |
|   | acetone | 45 | | | |
| 46 | acetone | 41 | 110 | 73 | 46 |
|   | EPW | 82 | | | |
| 47 | acetone | 74 | | 77 | |
|   | EPW | 69 | | | |

TABLE VIII-continued

| | | TPA - Route of Drug Administration | | | |
|---|---|---|---|---|---|
| Compound of Example No. | | Topical | | Subcutaneous | |
| | vehicle | % Inhibition at 200 µg | IC$_{50}$ | % Inhibition at 50 m/kg | ED$_{50}$ mg/kg |
| 48 | | | | 58 | |
| 50 | | | | 78 | 19 |
| 51 | | 55 | | 76 | |

EXAMPLE 66

The compounds of the invention are further tested in the rat carrageenan paw edema assay to determine their ability to inhibit the acute inflammatory response.

This assay is carried out as follows:

140–180 g Male Sprague-Dawley rats, in groups of 6 animals are injected subcutaneously in the right paw with 0.1 mL of 1% carrageenan at zero time. Mercury plethysmographic readings (mL) of the paw are made at zero time and 3 hours later. Test compounds are suspended or dissolved in 0.5% methylcellulose and given perorally 1 hour prior to carrageenan administration.

The increase in paw volume (edema in mL) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral ED$_{50}$ (95% C.L.) mg/kg |
|---|---|
| Indomethacin | 3.7 (0.6, 23.8) |
| Aspirin | 145.4 (33.1, 645.6) |
| Phenylbutazone | 26.2 (2.3, 291.0) |

When tested in this assay, a compound of the invention and the anti-inflammatory drug etodolac gave the following results:

TABLE IX

| Compound of Example No. | Dose* (mg/kg) | % Inhibition 50 mg/kg (peroral) |
|---|---|---|
| 1 | 50 | 40 |
| 6 | 50 | 31 |
| 7 | 50 | 47 |
| 9 | 100 | 41 |
| 12 | 50 | 30 |

*administered perorally

The results show that the compounds tested have activity in the rat carrageenan paw edema assay, evidencing an effect on the acute inflammatory response.

What is claimed is:

1. A compound having the formula

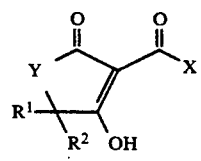

wherein
X is —CH$_2$R;

R is —(CH$_2$)$_a$(CH=CHCH$_2$)$_c$(CH$_2$)$_d$CH$_3$, —(CH$_2$)$_a$(C≡CCH$_2$)$_c$(CH$_2$)$_d$CH$_3$, or —(CH$_2$)$_b$CH=CHR$^3$;

Y is —O— or —S—;

R$^1$ and R$^2$ are each, independently, hydrogen or lower alkyl;

R$^3$ is phenyl or phenyl optionally mono- or disubstituted independently by alkyl of 1–7 carbon atoms, —C(CH$_3$)$_3$, —C(CH$_3$)$_2$CH$_2$C(CH$_3$)$_3$, —C(CH$_3$)$_2$CH$_2$CH$_3$, haloloweralkyl, perfluoroalkyl, lower alkoxy, aryl alkoxy, halo or nitro;

a is 0–8;
b is 1–10 when Y=S, and 2–10 when Y=O;
c is 1–3;
d is 0–9; and
e is 3–18.

2. A compound of claim 1 having the name (Z)-4-hydroxy-3-(1-oxo-9-octadecenyl)-2(5H)-furanone.

3. A compound of claim 1 having the name (Z,Z)-4-hydroxy-3-(1-oxo-9,12-octadecadienyl)-2(5H)-furanone.

4. A compound of claim 1 having the name (Z,Z,Z)-4-hydroxy-3-(1-oxo-9,12,15-octadecatrienyl)-2(5H)-furanone.

5. A compound of claim 1 having the name (Z)-4-hydroxy-5,5-dimethyl-3-(1-oxo-9-octadecenyl)-2(5H)-furanone.

6. A compound of claim 1 having the name (Z)-4-hydroxy-3-(1-oxo-6-octadecenyl)-2(5H)-furanone.

7. A compound of claim 1 having the name (Z,Z,Z)-4-hydroxy-3-(1-oxo-6,9,12-octadecatrienyl)-2(5H)-furanone.

8. A compound of claim 1 having the name 4-hydroxy-3-((Z)-1-oxo-10-tetradecenyl)-2(5H)-furanone.

9. A compound of claim 1 having the name 4-hydroxy-3-((Z)-1-oxo-9-tetradecenyl)-2(5H)-furanone.

10. A compound of claim 1 having the name 4-hydroxy-3-((Z)-1-oxo-9-hexadecenyl)-2(5H)-furanone.

11. A compound of claim 1 having the name 4-hydroxy-3-(1-oxo-9-octadecynyl)-2(5H)-furanone.

12. A compound of claim 1 having the name 4-hydroxy-3-(1-oxooctadecyl)-2(5H)-furanone.

13. A compound of claim 1 having the name 3-[(Z)-10-(4-chlorophenyl)-1-oxo-9-decenyl]-4-hydroxy-2(5H)-furanone.

14. A compound of claim 1 having the name 4-hydroxy-3-((E)-1-oxo-9-octadecenyl)-2(5H)-furanone.

15. A compound of claim 1 having the name 4-hydroxy-3-[10-(4-chlorophenyl)-1-oxodecyl]-2(5H)-furanone.

16. A compound of claim 1 having the name 4-hydroxy-3-[10-(3,4-dichlorophenyl)-1-oxodecyl]-2(5H)-furanone.

17. A compound of claim 1 having the name 4-hydroxy-3-[10-[4-(1,1-dimethylethyl)phenyl]1-oxodecyl]-2(5H)-furanone.

18. A compound of claim 1 having the name 4-hydroxy-3-[10-(4-bromophenyl)-1-oxodecyl]-2(5H)-furanone.

19. A compound of claim 1 having the name 4-hydroxy-3-[10-(4-trifluoromethyl)-phenyl]-2(5H)-furanone.

20. A compound of claim 1 having the name 4-hydroxy-3-[(Z,Z)-1-oxo-9,12-octadecadienyl]-2(5H)-thiophenone.

21. A compound of claim 1 having the name 4-hydroxy-3-[(Z)-1-oxo-9-octadecenyl]-2(5H)-thiophenone.

22. A compound of claim 1 having the name 4-hydroxy-3-[(Z)-1-oxo-9-tetradecenyl]-2(5H)-thiophenone.

23. A compound of claim 1 having the name 4-hydroxy-3-[(Z,Z,Z)-1-oxo-6,9,12-octadecatrienyl]-2(5H)-thiophenone.

24. A compound of claim 1 having the name 4-hydroxy-3-[(Z)-1-oxo-6-octadecenyl]-2(5H)-thiophenone.

25. A method for treating immunoinflammatory conditions in mammals which comprises administering to a mammal so afflicted an effective amount of a compound having the formula

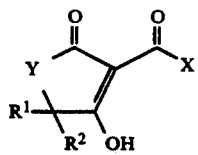

wherein
Y is —O— or —S—;
X is —(CH$_2$)$_a$CH$_3$, —(CH$_2$)$_b$Z or —(CH=CH)$_b$Z when Y=O, and —(CH$_2$)$_a$CH$_3$ when Y=S;

R$^1$ and R$^2$ are each, independently, hydrogen or lower alkyl;

Z is phenyl or phenyl optionally mono- or disubstituted independently by alkyl of 1–7 carbon atoms, haloloweralkyl, perfluoroalkyl, loweralkoxy, aralkoxy, halo or nitro;

a is 0–20 when Y=O, and a is 1–3 when Y=S; and
b is 1–2.

26. The method of claim 25 wherein the compound has the name 4-hydroxy-3-(1-oxodecyl)-2(5H)-furanone.

27. The method of claim 25 wherein the compound has the name 4-hydroxy-3-(1-oxo-3-phenylpropyl)-2(5H)-furanone.

28. The method of claim 25 wherein the compound has the name (E)-4-hydroxy-3-(3-(4-methoxyphenyl)-1-oxo-2-propenyl)-2 (5H)-furanone.

29. The method of claim 25 wherein the compound has the name (E)-4-hydroxy-3-(3-(4-chlorophenyl)-1-oxo-2-propenyl)-2(5H)-furanone.

30. The method of claim 25 wherein the compound has the name (E)-4-hydroxy-3-(3-(phenyl)-1-oxo-2-propenyl)-2(5H)-furanone.

31. The method of claim 25 wherein the compound has the name (E)-4-hydroxy-3-(1-oxo-3-(3-(trifluoromethyl)phenyl)-2-propenyl)-2 (5H)-furanone.

32. The method of claim 25 wherein the compound has the name 4-hydroxy-3-(1-oxoeicosanoyl)-2(5H)-furanone.

33. The method of claim 25 wherein the compound has the name (E)-4-hydroxy-3-(3-(3-nitrophenyl)-1-oxo-2-propenyl)-2 (5H)-furanone.

34. The method of claim 25 wherein the compound has the name (E)-3-(3-(2,5-dimethoxyphenyl)-1-oxo-2-propenyl)-4-hydroxy-2 (5H)-furanone.

35. The method of claim 25 wherein the compound has the name (E)-3-(3-(3,4-dimethoxyphenyl)-1-oxo-2-propenyl)-4-hydroxy-2 (5H)-furanone.

36. The method of claim 25 wherein the compound has the name (E)-3-(3-(3,4-dimethoxyphenyl)-1-oxo-2-propenyl)-4-hydroxy-2 (5H)-furanone.

37. The method of claim 25 wherein the compound has the name 4-hydroxy-3-[1-oxohexadecyl]-2(5H)-furanone.

* * * * *